(12) United States Patent
Wang et al.

(10) Patent No.: US 10,464,953 B2
(45) Date of Patent: Nov. 5, 2019

(54) CARBON BRIDGED AMINOSILANE COMPOUNDS FOR HIGH GROWTH RATE SILICON-CONTAINING FILMS

(71) Applicant: Versum Materials US, LLC, Tempe, AZ (US)

(72) Inventors: Meiliang Wang, Carlsbad, CA (US); Xinjian Lei, Vista, CA (US); Manchao Xiao, San Diego, CA (US); Suresh Kalpatu Rajaraman, San Marcos, CA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 90 days.

(21) Appl. No.: 15/725,122

(22) Filed: Oct. 4, 2017

(65) Prior Publication Data
US 2018/0105541 A1    Apr. 19, 2018

Related U.S. Application Data

(60) Provisional application No. 62/408,310, filed on Oct. 14, 2016.

(51) Int. Cl.
| | | |
|---|---|---|
| *H01L 21/31* | (2006.01) | |
| *C07F 7/10* | (2006.01) | |
| *C23C 16/40* | (2006.01) | |
| *C23C 16/44* | (2006.01) | |
| *C23C 16/455* | (2006.01) | |
| *C23C 16/50* | (2006.01) | |
| *H01L 21/02* | (2006.01) | |

(52) U.S. Cl.
CPC .............. *C07F 7/10* (2013.01); *C23C 16/401* (2013.01); *C23C 16/4408* (2013.01); *C23C 16/45536* (2013.01); *C23C 16/45542* (2013.01); *C23C 16/45553* (2013.01); *C23C 16/50* (2013.01); *H01L 21/0228* (2013.01); *H01L 21/02126* (2013.01); *H01L 21/02164* (2013.01); *H01L 21/02211* (2013.01); *H01L 21/02219* (2013.01); *H01L 21/02274* (2013.01)

(58) Field of Classification Search
CPC ........... H01L 21/02126; H01L 21/0214; H01L 21/02164; H01L 21/02167; H01L 21/0217; H01L 21/02211; H01L 21/02219; H01L 21/0262; H01L 21/02271; H01L 21/02274; H01L 21/0228; H01L 21/02532; H01L 21/02592; H01L 21/02598; C23C 16/24; C23C 16/401; C23C 16/4408; C23C 16/45536; C23C 16/45542; C23C 16/45553; C23C 16/50; C07F 7/10
USPC ................ 438/778, 786, 789, 790, 793, 794
See application file for complete search history.

(56) References Cited

U.S. PATENT DOCUMENTS

| | | | |
|---|---|---|---|
| 5,424,095 A | 6/1995 | Clark et al. | |
| 6,992,019 B2 | 1/2006 | Lee et al. | |
| 7,084,076 B2 | 8/2006 | Park et al. | |
| 9,245,740 B2 | 1/2016 | Jang et al. | |
| 2012/0291321 A1 | 11/2012 | Spiro | |
| 2013/0295779 A1 | 11/2013 | Chandra et al. | |
| 2014/0287164 A1* | 9/2014 | Xiao | C07F 7/0896 427/579 |
| 2015/0087139 A1* | 3/2015 | O'Neill | C23C 16/24 438/482 |
| 2015/0376211 A1 | 12/2015 | Girard et al. | |

FOREIGN PATENT DOCUMENTS

| | | |
|---|---|---|
| CN | 104672265 | 6/2015 |
| JP | 2010225663 A2 | 10/2010 |
| JP | 2010275602 A2 | 12/2010 |
| WO | 2015105337 A1 | 7/2015 |
| WO | 2015190749 A1 | 12/2015 |

OTHER PUBLICATIONS

Burton, B. B., et al., "SiO2 Atomic Layer Deposition Using Tris(dimethylamino)silane and Hydrogen Peroxide Studied by in Situ Transmission FTIR Spectroscopy," the Journal of Physical Chemistry (2009), vol. 113, pp. 8249-8257.
Abel, E. W., et al., "Some New Alkylaminosilanes," J. Chem. soc., (1964), vol. 26, pp. 1528-1530.

* cited by examiner

*Primary Examiner* — Brook Kebede
(74) *Attorney, Agent, or Firm* — Joseph D. Rossi

(57) ABSTRACT

Described herein are compositions and methods for forming silicon oxide films. In one aspect, the film is deposited from at least one precursor, wherein the at least one precursor has a structure represented by Formula A:

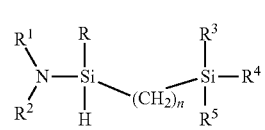

wherein R, $R^1$, $R^2$, $R^3$, $R^4$, and $R^5$ are defined herein.

20 Claims, 2 Drawing Sheets

CARBON BRIDGED AMINOSILANE COMPOUNDS FOR HIGH GROWTH RATE SILICON-CONTAINING FILMS

CROSS-REFERENCE TO RELATED APPLICATIONS

This application claim priority under 35 U.S.C. § 119(e) to U.S. provisional patent application No. 62/408,310, filed on Oct. 14, 2016, the entirety of which is incorporated herein by reference.

BACKGROUND OF THE INVENTION

Described herein is a composition and method for the formation of a silicon and oxygen containing film. More specifically, described herein is a composition and method for formation of a stoichiometric or a non-stoichiometric silicon oxide film or material at one or more deposition temperatures of about 300° C. or less, or ranging from about 25° C. to about 600° C.

Atomic Layer Deposition (ALD) and Plasma Enhanced Atomic Layer Deposition (PEALD) are processes used to deposit silicon oxide conformal films at low temperatures (<500° C.). In both ALD and PEALD processes, the precursor and reactive gas (such as oxygen or ozone) are separately pulsed in certain number of cycles to form a monolayer of silicon oxide at each cycle. However, silicon oxide deposited at low temperatures using these processes may contain levels of impurities such as, without limitation, nitrogen (N) which may be detrimental in certain semiconductor applications. To remedy this, one possible solution is to increase the deposition temperature to 500° C. or greater. However, at these higher temperatures, conventional precursors employed by semi-conductor industries tend to self-react, thermally decompose, and deposit in a chemical vapor deposition (CVD) mode rather than an ALD mode. The CVD mode deposition has reduced conformality compared to ALD deposition, especially for high aspect ratio structures which are needed in many semiconductor applications. In addition, the CVD mode deposition has less control of film or material thickness than the ALD mode deposition.

The reference article entitled "Some New Alkylaminosilanes," Abel, E. W. et al., J. Chem. Soc., (1964), Vol. 26, pp. 1528-1530 describes the preparation of various aminosilane compounds such as $Me_3SiNHBu$-iso, $Me_3SiNHBu$-sec, $Me_3SiN(Pr$-iso$)_2$, and $Me_3SiN(Bu$-sec$)_2$ wherein Me=methyl, Bu-sec=sec-butyl, and Pr-iso=isopropyl from the direct interaction of trimethylchlorosilane ($Me_3SiCl$) and the appropriate amine.

The reference article entitled "$SiO_2$ Atomic Layer Deposition Using Tris(dimethylamino)silane and Hydrogen Peroxide Studied by in Situ Transmission FTIR Spectroscopy, Burton, B. B., et al., The Journal of Physical Chemistry (2009), Vol. 113, pp. 8249-57 describes the atomic layer deposition (ALD) of silicon dioxide ($SiO_2$) using a variety of silicon precursors with $H_2O_2$ as the oxidant. The silicon precursors were (N,N-dimethylamino)trimethylsilane) $(CH_3)_3SiN(CH_3)_2$, vinyltrimethoxysilane $CH_2CHSi(OCH_3)_3$, trivinylmethoxysilane $(CH_2CH)_3SiOCH_3$, tetrakis(dimethylamino)silane $Si(N(CH_3)_2)_4$, and tris(dimethylamino)silane (TDMAS) $SiH(N(CH_3)_2)_3$. TDMAS was determined to be the most effective of these precursors. However, additional studies determined that SiH* surface species from TDMAS were difficult to remove using only $H_2O$. Subsequent studies utilized TDMAS and $H_2O_2$ as the oxidant and explored $SiO_2$ ALD in the temperature range of 150-550° C. The exposures required for the TDMAS and $H_2O_2$ surface reactions to reach completion and were monitored using in situ FTIR spectroscopy. The FTIR vibrational spectra following the TDMAS exposures showed a loss of absorbance for O—H stretching vibrations and a gain of absorbance for C—Hx and Si—H stretching vibrations. The FTIR vibrational spectra following the $H_2O_2$ exposures displayed a loss of absorbance for C—Hx and Si—H stretching vibrations and an increase of absorbance for the O—H stretching vibrations. The SiH* surface species were completely removed only at temperatures>450° C. The bulk vibrational modes of $SiO_2$ were observed between 1000-1250 $cm^{-1}$ and grew progressively with number of TDMAS and $H_2O_2$ reaction cycles. Transmission electron microscopy (TEM) was performed after 50 TDMAS and $H_2O_2$ reaction cycles on $ZrO_2$ nanoparticles at temperatures between 150-550° C. The film thickness was determined by TEM at each temperature to obtain the $SiO_2$ ALD growth rate. The growth per cycle varied from 0.8 Å/cycle at 150° C. to 1.8 Å/cycle at 550° C. and was correlated with the removal of the SiH* surface species. $SiO_2$ ALD using TDMAS and $H_2O_2$ should be valuable for $SiO_2$ ALD at temperatures>450° C.

JP 2010275602 and JP 2010225663 disclose the use of a raw material to form a Si containing thin film such as, silicon oxide, by a chemical vapor deposition (CVD) process at a temperature range of from 300-500° C. The raw material is an organic silicon compound, represented by formula: (a) $HSi(CH_3)(R^1)(NR^2R^3)$, wherein, $R^1$ represents $NR^4R^5$ or a 1C-5C alkyl group; $R^2$ and $R^4$ each represent a 1C-5C alkyl group or hydrogen atom; and $R^3$ and $R^5$ each represent a 1C-5C alkyl group); or (b) $HSiCl(NR^1R^2)(NR^3R^4)$, wherein $R^1$ and $R^3$ independently represent an alkyl group having 1 to 4 carbon atoms, or a hydrogen atom; and $R^2$ and $R^4$ independently represent an alkyl group having 1 to 4 carbon atoms. The organic silicon compounds contained H—Si bonds.

U.S. Pat. No. 5,424,095 describes a method to reduce the rate of coke formation during the industrial pyrolysis of hydrocarbons, the interior surface of a reactor is coated with a uniform layer of a ceramic material, the layer being deposited by thermal decomposition of a non-alkoxylated organosilicon precursor in the vapor phase, in a steam containing gas atmosphere in order to form oxide ceramics.

U.S. 2012/0291321 describes a PECVD process for forming a high-quality Si carbonitride barrier dielectric film between a dielectric film and a metal interconnect of an integrated circuit substrate, comprising the steps of: providing an integrated circuit substrate having a dielectric film or a metal interconnect; contacting the substrate with a barrier dielectric film precursor comprising: $R_xR_y(NRR')_zSi$ wherein R, R', R and R' are each individually selected from H, linear or branched saturated or unsaturated alkyl, or aromatic group; wherein x+y+z=4; z=1 to 3; but R, R' cannot both be H; and where z=1 or 2 then each of x and y are at least 1; forming the Si carbonitride barrier dielectric film with C/Si ratio>0.8 and a N/Si ratio>0.2 on the integrated circuit substrate.

U.S. 2013/0295779 describes an atomic layer deposition (ALD) process for forming a silicon oxide film at a deposition temperature>500° C. using silicon precursors having the following formula:

$$R^1R^2{}_mSi(NR^3R^4)_nX_p \qquad \text{I.}$$

wherein $R^1$, $R^2$, and $R^3$ are each independently selected from hydrogen, a linear or branched $C_1$ to $C_{10}$ alkyl group, and a $C_6$ to $C_{10}$ aryl group; $R^4$ is selected from, a linear or branched $C_1$ to $C_{10}$ alkyl group, and a $C_6$ to $C_{10}$ aryl group, a $C_3$ to $C_{10}$ alkylsilyl group; wherein $R^3$ and $R^4$ are linked to form a cyclic ring structure or $R^3$ and $R^4$ are not linked to form a cyclic ring structure; X is a halide selected from the group consisting of Cl, Br and I; m is 0 to 3; n is 0 to 2; and p is 0 to 2 and m+n+p=3; and $$R^1R^2{}_m Si(OR^3)_n(OR^4)_q X_p \qquad \text{II.}$$

wherein $R^1$ and $R^2$ are each independently selected from hydrogen, a linear or branched $C_1$ to $C_{10}$ alkyl group, and a $C_6$ to $C_{10}$ aryl group; $R^3$ and $R^4$ are each independently selected from a linear or branched $C_1$ to $C_{10}$ alkyl group, and a $C_6$ to $C_{10}$ aryl group;
wherein $R^3$ and $R^4$ are linked to form a cyclic ring structure or $R^3$ and $R^4$ are not linked to form a cyclic ring structure; X is a halide atom selected from the group consisting of Cl, Br and I; m is 0 to 3; n is 0 to 2; q is 0 to 2 and p is 0 to 2 and m+n+q+p=3

U.S. Pat. No. 7,084,076 discloses a halogenated siloxane such as hexachlorodisiloxane (HCDSO) that is used in conjunction with pyridine as a catalyst for ALD deposition below 500° C. to form silicon dioxide.

U.S. Pat. No. 6,992,019 discloses a method for catalyst-assisted atomic layer deposition (ALD) to form a silicon dioxide layer having superior properties on a semiconductor substrate by using a first reactant component consisting of a silicon compound having at least two silicon atoms, or using a tertiary aliphatic amine as the catalyst component, or both in combination, together with related purging methods and sequencing. The precursor used is hexachlorodisilane. The deposition temperature is between 25-150° C.

WO 2015/0105337 discloses novel trisilyl amine derivatives and a method for formation of silicon containing thin films, wherein the trisilyl amine derivatives are having thermal stability, high volatility, and high reactivity and being present in a liquid state at room temperature and under pressure where handling is possible, may form a high purity silicon containing thin film having excellent physical and electric properties by various deposition methods.

WO 2015/0190749 discloses novel amino-silyl amine compounds, $(Me_2NSiR^3R^4)N(SiHR^1R^2)_2$ ($R^1$-$R^4$=$C_{1-3}$ alkyl, $C_{2-3}$ alkenyl, $C_{2-3}$ alkynyl, $C_{3-7}$ cycloalkyl, $C_{6-12}$ aryl, etc.), and a method of a dielectric film containing Si—N bond. Since the amino-silyl amine compd. according to the present invention, which is a thermally stable and highly volatile compd., may be treated at room temp. and used as a liq. state compd. at room temp. and pressure, the present invention provides a method of a high purity dielectric film containing a Si—N bond even at a low temp. and plasma condition by using at. layer deposition (PEALD).

U.S. Pat. No. 9,245,740 B provides novel amino-silyl amine compounds, a method for preparing the same, and a silicon-containing thin-film using the same, wherein the amino-silyl amine compd. has thermal stability and high volatility and is maintained in a liquid state at room temp. and under a pressure where handling is easy to thereby form a silicon-containing thin-film having high purity and excellent physical and electric properties by various deposition methods.

U.S. 2015/0376211 discloses mono-substituted TSA precursor Si-containing film forming compositions are disclosed. The precursors have the formula: $(SiH_3)_2N$—$SiH_2$—X, wherein X is selected from a halogen atom; an isocyanato group; an amino group; an N-containing C4-C10 saturated or unsaturated heterocycle; or an alkoxy group. Methods for forming the Si-containing film using the disclosed mono-substituted TSA precursor are also disclosed.

Despite these developments there is still a need to develop a process for forming a silicon oxide film having at least one or more of the following attributes: a density of about 1.80 g/cm³ or greater, preferably 2.0 g/cm³ or greater, most preferably 2.2 g/cm³ or greater, a growth rate of 1.5 Å/cycle or greater, preferably 2.0 Å/cycle or greater, most preferably 2.4 Å/cycle or greater, low chemical impurity, and/or high conformality in a thermal atomic layer deposition, a plasma enhanced atomic layer deposition (ALD) process or a plasma enhanced ALD-like process using cheaper, reactive, and more stable silicon precursor compounds. In addition, there is a need to develop precursors that can provide tunable films for example, ranging from silicon oxide to carbon doped silicon oxide.

BRIEF SUMMARY OF THE INVENTION

Described herein is a process for the deposition of a stoichiometric or nonstoichiometric silicon oxide material or film, such as without limitation, a silicon oxide, a carbon doped silicon oxide, a silicon oxynitride film, or a carbon doped silicon oxynitride film at relatively low temperatures, e.g., at one or more temperatures of 600° C. or lower, in a plasma enhanced ALD, plasma enhanced cyclic chemical vapor deposition (PECCVD), a plasma enhanced ALD-like process, or an ALD process with oxygen reactant source.

In one aspect, there is provided a method for depositing a film comprising silicon and oxygen onto a substrate, which comprises the steps of:
  a) providing a substrate in a reactor;
  b) introducing into the reactor at least one silicon precursor compound comprising at least one organoaminocarbosilane compound, wherein the at least one organoaminocarbosilane compound has at least one $SiH_2$ or SiMeH group and is represented by the structure of Formula A:

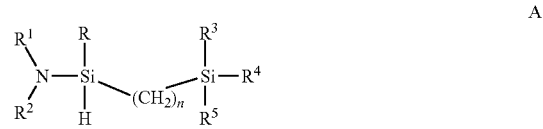

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, a $C_6$ to $C_{10}$ aryl group, a $C_3$ to $C_{10}$ cyclic alkyl group, a branched $C_4$ to $C_{10}$ cyclic alkyl group, a $C_3$ to $C_{10}$ cyclic alkenyl group, a branched $C_4$ to $C_{10}$ cyclic alkenyl group, a $C_3$ to $C_6$ cyclic alkynyl group, a branched $C_3$ to $C_6$ cyclic alkynyl group, a $C_1$ to $C_6$ dialkylamino group, a $C_1$ to $C_6$ alkylamino group; $R^{2-5}$ are independently selected from the group consisting of hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, a $C_6$ to $C_{10}$ aryl group, a $C_3$ to $C_{10}$ cyclic alkyl group, a branched $C_4$ to $C_{10}$ cyclic alkyl group, a $C_3$ to $C_{10}$ cyclic alkenyl group, a branched $C_4$ to $C_{10}$ cyclic alkenyl group, a $C_3$ to $C_6$ cyclic alkynyl group, a branched $C_3$ to $C_6$ cyclic alkynyl group, and a $C_4$ to $C_{10}$ aryl group; and R is selected from hydrogen or methyl; n=2 or 3; and provided that R and $R^{3-5}$ cannot be all hydrogen;
  c) purging the reactor with a purge gas;
  d) introducing an oxygen-containing source into the reactor; and e) purging the reactor with the purge gas,
wherein the steps b through e are repeated until a desired thickness of film is deposited; and wherein the method is conducted at one or more temperatures ranging from about 25° C. to 600° C.

In preferred embodiments, the oxygen-containing source is a source selected from the group consisting of an oxygen plasma, ozone, a water vapor, water vapor plasma, nitrogen oxide (e.g., $N_2O$, NO, $NO_2$) plasma with or without inert gas, a carbon oxide (e.g., $CO_2$, CO) plasma and combinations thereof. In certain embodiments, the oxygen source further comprises an inert gas. In these embodiments, the inert gas is selected from the group consisting of argon, helium, nitrogen, hydrogen, and combinations thereof. In an alternative embodiment, the oxygen source does not comprise an inert gas. In yet another embodiment, the oxygen-containing source comprises nitrogen which reacts with the reagents under plasma conditions to provide a silicon oxynitride film.

In preferred embodiments, the oxygen-containing plasma source is selected from the group consisting of oxygen plasma with or without inert gas, water vapor plasma with or without inert gas, nitrogen oxides ($N_2O$, NO, $NO_2$) plasma with or without inert gas, carbon oxides ($CO_2$, CO) plasma with or without inert gas, and combinations thereof. In certain embodiments, the oxygen-containing plasma source further comprises an inert gas. In these embodiments, the inert gas is selected from the group consisting of argon, helium, nitrogen, hydrogen, or combinations thereof. In an alternative embodiment, the oxygen-containing plasma source does not comprise an inert gas.

In one aspect, the invention relates to a composition for depositing a film selected from a silicon oxide or a carbon doped silicon oxide film using a vapor deposition process, wherein the composition comprises at least one silicon precursor compound comprising at least one organoaminocarbosilane compound, wherein the at least one organoaminocarbosilane compound has at least one $SiH_2$ or SiMeH group and is represented by the structure of Formula A:

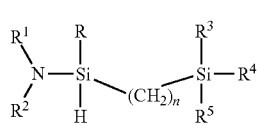

A wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, a $C_6$ to $C_{10}$ aryl group, a $C_3$ to $C_{10}$ cyclic alkyl group, a branched $C_4$ to $C_{10}$ cyclic alkyl group, a $C_3$ to $C_{10}$ cyclic alkenyl group, a branched $C_4$ to $C_{10}$ cyclic alkenyl group, a $C_3$ to $C_6$ cyclic alkynyl group, a branched $C_3$ to $C_6$ cyclic alkynyl group, a $C_1$ to $C_6$ dialkylamino group, a $C_1$ to $C_6$ alkylamino group; $R^{2-5}$ are independently selected from the group consisting of hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, a $C_6$ to $C_{10}$ aryl group, a $C_3$ to $C_{10}$ cyclic alkyl group, a branched $C_4$ to $C_{10}$ cyclic alkyl group, a $C_3$ to $C_{10}$ cyclic alkenyl group, a branched $C_4$ to $C_{10}$ cyclic alkenyl group, a $C_3$ to $C_6$ cyclic alkynyl group, a branched $C_3$ to $C_6$ cyclic alkynyl group, and a $C_4$ to $C_{10}$ aryl group; and R is selected from hydrogen or methyl; n=2 or 3; and provided that R and $R^{3-5}$ cannot be all hydrogen.

In another aspect, the invention relates to a silicon oxide film comprising at least one of the following characteristics: a density of at least about 2.1 $g/cm^3$; a wet etch rate that is less than about 2.5 Å/s as measured in a solution of 1:100 of HF to water dilute HF (0.5 wt. % dHF) acid; an electrical leakage of less than about 1 e-8 $A/cm^2$ up to 6 MV/cm; and a hydrogen impurity of less than about 4 e21 $at/cm^3$ as measured by SIMS.

The embodiments of the invention can be used alone or in combinations with each other.

DETAILED DESCRIPTION OF THE INVENTION

Figure 1:
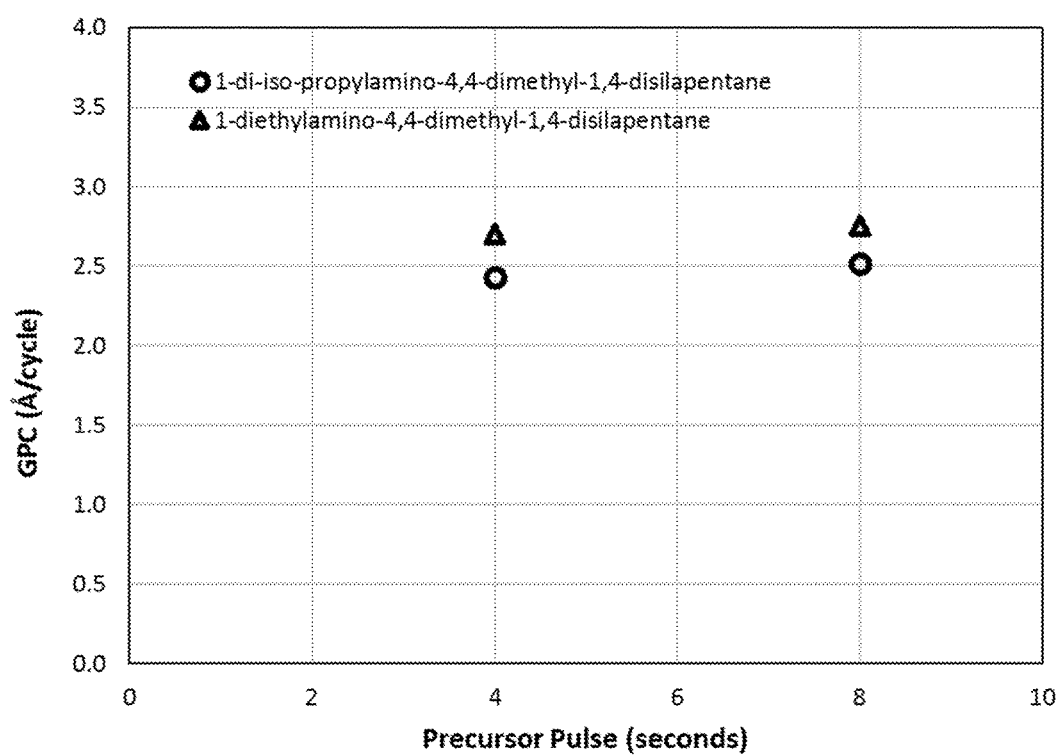
FIG. 1 provides growth rate per cycle (GPC) versus precursor pulse time using 1-di-iso-propylamino-4,4-dimethyl-1,4-disilapentane and oxygen plasma at temperature of 100° C. described in Example 3, and 1-diethylamino-4,4-dimethyl-1,4-disilapentane and oxygen plasma at temperature of 100° C. described in Example 4, demonstrating both 1-di-iso-propylamino-4,4-dimethyl-1,4-disilapentane and 1-diethylamino-4,4-dimethyl-1,4-disilapentane are suitable for ALD or PEALD application.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Described herein are methods for forming a stoichiometric or nonstoichiometric film or material comprising silicon and oxygen such as, without limitation, a silicon oxide, a carbon-doped silicon oxide film, a silicon oxynitride, a carbon-doped silicon oxynitride film or combinations thereof with one or more temperatures, of about 300° C. or less in some embodiments, or from about 25° C. to about 600° C. in other embodiments. The films described herein are deposited in a deposition process such as an atomic layer deposition (ALD) or in an ALD-like process such as, without limitation, a plasma enhanced ALD or a plasma enhanced cyclic chemical vapor deposition process (CCVD). The low temperature deposition (e.g., one or more deposition temperatures ranging from about ambient temperature (about 25° C.) to about 600° C.) methods described herein provide films or materials that exhibit at least one or more of the following advantages: a density of about 2.1 g/cm$^3$ or greater, low chemical impurity, high conformality in a thermal atomic layer deposition, a plasma enhanced atomic layer deposition (ALD) process or a plasma enhanced ALD-like process, an ability to adjust carbon content in the resulting film; and/or films have an etching rate of 5 Angstroms per second (Å/sec) or less when measured in 0.5 wt. % dilute HF. For carbon-doped silicon oxide films, greater than 1 wt. % carbon is desired to tune the etch rate to values below 2 Å/sec in addition to other characteristics such as, without limitation, a density of about 1.8 g/cm$^3$ or greater or about 2.0 g/cm$^3$ or greater.

The instant invention can be practiced using equipment known in the art. For example, the inventive method can use a reactor that is conventional in the semiconductor manufacturing art.

In one aspect, the composition of the present invention comprises at least one organoaminocarbosilane compound as a silicon precursor for use in vapor deposition, wherein the at least one organoaminocarbosilane compound has at least one SiH$_2$ or SiMeH group and is represented by the structure of Formula A:

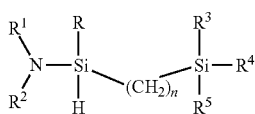

A wherein R$^1$ is selected from a linear or branched C$_1$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, a C$_6$ to C$_{10}$ aryl group, a C$_3$ to C$_{10}$ cyclic alkyl group, a branched C$_4$ to C$_{10}$ cyclic alkyl group, a C$_3$ to C$_{10}$ cyclic alkenyl group, a branched C$_4$ to C$_{10}$ cyclic alkenyl group, a C$_3$ to C$_6$ cyclic alkynyl group, a branched C$_3$ to C$_6$ cyclic alkynyl group, a C$_1$ to C$_6$ dialkylamino group, a C$_1$ to C$_6$ alkylamino group; R$^{2-5}$ are independently selected from the group consisting of hydrogen, a linear or branched C$_1$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, a C$_6$ to C$_{10}$ aryl group, a C$_3$ to C$_{10}$ cyclic alkyl group, a branched C$_4$ to C$_{10}$ cyclic alkyl group, a C$_3$ to C$_{10}$ cyclic alkenyl group, a branched C$_4$ to C$_{10}$ cyclic alkenyl group, a C$_3$ to C$_6$ cyclic alkynyl group, a branched C$_3$ to C$_6$ cyclic alkynyl group, and a C$_4$ to C$_{10}$ aryl group; and R is selected from hydrogen or methyl; n=2 or 3; and provided that R and R$^{3-5}$ cannot be all hydrogen.

In certain embodiments of Formula A, R$^1$ and R$^2$ are linked together to form a ring. In one particular embodiment, R$^1$ and R$^2$ are selected from a linear or a branched C$_3$ to C$_6$ alkyl group and are linked to form a cyclic ring. In alternative embodiments of Formula A, R$^1$ and R$^2$ are not linked together to form a ring. In certain embodiments of Formula A, R$^1$ and R$^2$ are the same. In other embodiments, R$^1$ and R$^2$ are different. In one particular embodiment, R$^1$ and R$^2$ are independently selected from linear or branched C$_1$ to C$_{10}$ alkyl groups such as methyl, ethyl, iso-propyl, sec-butyl, tert-butyl; R$^{3-5}$ are independently selected from hydrogen or C$_1$ alkyl, i.e. methyl.

The organoaminocarbosilane precursors described herein exhibit a balance of reactivity and stability that makes them ideally suitable as CVD or ALD precursors in microelectronic device manufacturing processes. With regard to reactivity, the organoaminocarbosilane in this invention has only one organoamino group which helps formation of Si—O—SH$_2$ or Si—O—SHR (preferable R=Me) linkage upon reacting the organoaminocarbosilane precursors with hydroxyl surface during ALD process. Without intending to be bound by particular theory, it is believed that the smaller footprint of SiH$_2$ or SHMe, especially SiH$_2$ allows more silicon-containing fragments with Si—(CH$_2$)$_2$—Si or Si—(CH$_2$)$_3$—Si linkage being anchored, thus providing higher growth rate per cycle compared to conventional silicon precursors having only silicon atom. Certain precursors may have boiling points that are too high to be vaporized and delivered to the reactor to be deposited as a film on a substrate, so it is preferable to select smaller organoamino groups as well as smaller alkyl to provide precursors having boiling point of 250° C. or less, preferably boiling point of 200° C. or less. Having two or more organoamino groups as disclosed in prior art can increase the boiling point significantly, precursors having higher relative boiling points require that the delivery container and lines need to be heated at or above the boiling point of the precursor under a given vacuum to prevent condensation or particles from forming in the container, lines, or both. With regard to stability, other precursors may form silane (SiH$_4$) or disilane (Si$_2$H$_6$) as they degrade. Silane is pyrophoric at room temperature or it can spontaneously combust which presents safety and handling issues. Moreover, the formation of silane or disilane and other by-products decreases the purity level of the precursor and changes as small as 1-2 wt. % in chemical purity may be considered unacceptable for reliable semiconductor manufacture. In certain embodiments, the organoaminocarbosilane precursors having Formula I described herein comprise 2% or less by weight, or 1 wt. % or less by weight, or 0.5 wt. % or less by weight of by-product after being stored for a time period of 6 months or greater, or one year or greater which is indicative of being shelf stable. In addition to the foregoing advantages, in certain embodiments, such as for depositing a silicon oxide or silicon nitride or silicon film using an ALD, ALD-like, PEALD, or CCVD deposition method, the organoaminocarbosilane precursor described herein may be able to deposit high density materials at relatively low deposition temperatures, e.g., 500° C. or less, or 400° C. or less, 300° C. or less, 200° C. or less, 100° C. or less, or 50° C. or less.

In another aspect, there is provided a composition comprising: (a) at least one organoaminocarbosilane compound having at least one $SiH_2$ or SiMeH group connected to an organoamino functionality comprising a compound represented by the following Formula A:

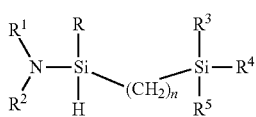

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, a $C_6$ to $C_{10}$ aryl group, a $C_3$ to $C_{10}$ cyclic alkyl group, a branched $C_4$ to $C_{10}$ cyclic alkyl group, a $C_3$ to $C_{10}$ cyclic alkenyl group, a branched $C_4$ to $C_{10}$ cyclic alkenyl group, a $C_3$ to $C_6$ cyclic alkynyl group, a branched $C_3$ to $C_6$ cyclic alkynyl group, a $C_1$ to $C_6$ dialkylamino group, a $C_1$ to $C_6$ alkylamino group; $R^{2-5}$ are independently selected from the group consisting of hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, a $C_6$ to $C_{10}$ aryl group, a $C_3$ to $C_{10}$ cyclic alkyl group, a branched $C_4$ to $C_{10}$ cyclic alkyl group, a $C_3$ to $C_{10}$ cyclic alkenyl group, a branched $C_4$ to $C_{10}$ cyclic alkenyl group, a $C_3$ to $C_6$ cyclic alkynyl group, a branched $C_3$ to $C_6$ cyclic alkynyl group, and a $C_4$ to $C_{10}$ aryl group; R is selected from hydrogen or methyl; n=2 or 3; and provided that R and $R^{3-5}$ cannot be all hydrogen; and (b) a solvent.

In certain embodiments of the composition described herein, exemplary solvents can include, without limitation, ether, tertiary amine, alkyl hydrocarbon, aromatic hydrocarbon, tertiary aminoether, and combinations thereof. In certain embodiments, the difference between the boiling point of the organoaminocarbosilane and the boiling point of the solvent is 40° C. or less. In certain embodiments of Formula A, $R^1$ and $R^2$ are linked together to form a ring. In one particular embodiment, $R^1$ and $R^2$ are selected from a linear or a branched $C_3$ to $C_6$ alkyl group and are linked to form a cyclic ring. In alternative embodiments of Formula A, $R^1$ and $R^2$ are not linked together to form a ring. In certain embodiments of Formula A, $R^1$ and $R^2$ are the same. In other embodiments, $R^1$ and $R^2$ are different. In one particular embodiment, $R^1$ and $R^2$ are independently selected from linear or branched $C_1$ to $C_{10}$ alkyl groups such as methyl, ethyl, iso-propyl, sec-butyl, tert-butyl; $R^{3-5}$ are independently selected from hydrogen or $C_1$ alkyl, i.e. methyl.

In another embodiment, the present invention provides a method for depositing a film comprising silicon and oxygen onto a substrate, which comprises the steps of:
a. providing a substrate in a reactor;
b. introducing into the reactor at least one silicon precursor having Formula A described herein;
c. purging the reactor with purge gas;
d. introducing an oxygen-containing source into the reactor; and
e. purging the reactor with a purge gas.

In the method described above, steps b through e are repeated until a desired thickness of film is deposited on the substrate.

In a preferred embodiment, the method of the present invention is conducted via an ALD process that uses an oxygen-containing source which comprises a plasma wherein the plasma can further comprise an inert gas such as one or more of the following: an oxygen plasma with or without inert gas, a water vapor plasma with or without inert gas, a nitrogen oxide (e.g., $N_2O$, NO, $NO_2$) plasma with or without inert gas, a carbon oxide (e.g., $CO_2$, CO) plasma with or without inert gas, and combinations thereof.

The oxygen-containing source can be generated in situ or, alternatively, remotely. In one particular embodiment, the oxygen-containing source comprises oxygen and is flowing, or introduced during method steps b through d, along with other reagents such as without limitation, the at least one silicon precursor and optionally an inert gas.

In one particular embodiment, $R^{2-5}$ in Formula A comprise a hydrogen or a methyl group. Further exemplary precursors represented by Formula A are listed in Table 1.

TABLE 1

Exemplary Organoaminocarbosilane Compounds of Formula A

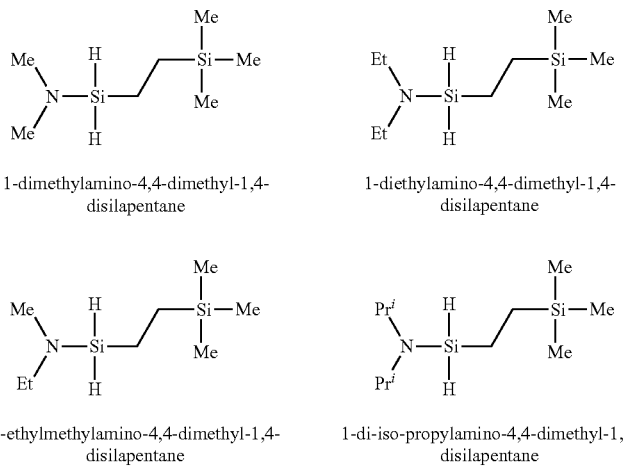

1-dimethylamino-4,4-dimethyl-1,4-disilapentane 1-diethylamino-4,4-dimethyl-1,4-disilapentane 1-ethylmethylamino-4,4-dimethyl-1,4-disilapentane 1-di-iso-propylamino-4,4-dimethyl-1,4-disilapentane TABLE 1-continued Exemplary Organoaminocarbosilane Compounds of Formula A 1-di-sec-butylamino-4,4-dimethyl-1,4-disilapentane 1-piperindino-sec-butylamino-4,4-dimethyl-1,4-disilapentane 1-piperindino-sec-butylamino-4,4-dimethyl-1,4-disilapentane 1-pyrrolidino-4,4-dimethyl-1,4-disilapentane 1-2,5-dimethylpyrrolidino-4,4-dimethyl-1,4-disilapentane 1-cyclohexylmethylamino-4,4-dimethyl-1,4-disilapentane 1-cyclohexylethylamino-4,4-dimethyl-1,4-disilapentane 1-cyclohexyl-iso-propylamino-4,4-dimethyl-1,4-disilapentane 1-dimethylamino-1-methyl-4,4-dimethyl-1,4-disilapentane 1-dimethylamino-1-methyl-4,4-diethyl-1,4-disilapentane 1-ethylamino-1-methyl-4,4-dimethyl-1,4-disilapentane 1-di-iso-propylamino-1-methyl-4,4-dimethyl-1,4-disilapentane TABLE 1-continued Exemplary Organoaminocarbosilane Compounds of Formula A 1-di-sec-butylamino-1-methyl-4,4-dimethyl-1,4-disilapentane 1-piperindino-1-methyl-4,4-dimethyl-1,4-disilapentane 1-2,5-dimethylpiperindino-sec-butylamino-1-methyl-4,4-dimethyl-1,4-disilapentane 1-pyrrolidino-1-methyl-4,4-dimethyl-1,4-disilapentane 1-2,5-dimethylpyrrolidino-1-methyl-4,4-dimethyl-1,4-disilapentane 1-cyclohexylmethylamino-1-methyl-4,4-dimethyl-1,4-disilapentane 1-cyclohexylethylamino-1-methyl-4,4-dimethyl-1,4-disilapentane 1-cyclohexyl-iso-propylamino-1-methyl-4,4-dimethyl-1,4-disilapentane 1-dimethylamino-5,5-dimethyl-1,5-disilahexane 1-diethylamino-5,5-dimethyl-1,5-disilahexane 1-ethylmethylamino-4,4-dimethyl-4,4-dimethyl-1,5-disilahexane 1-di-iso-propylamino-5,5-dimethyl-1,5-disilahexane TABLE 1-continued Exemplary Organoaminocarbosilane Compounds of Formula A

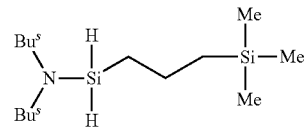

1-di-sec-butylamino-5,5-dimethyl-1,5-disilahexane

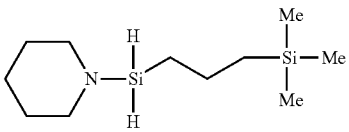

1-piperindino-5,5-dimethyl-1,5-disilahexane

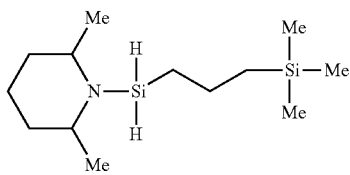

1-2,6-dimethylpiperindino-5,5-dimethyl-1,5-disilahexane

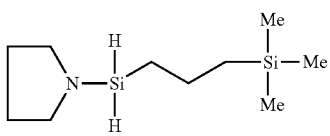

1-pyrrolidino-5,5-dimethyl-1,5-disilahexane

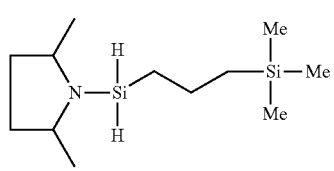

1-2,5-dimethylpyrrolidino-5,5-dimethyl-1,5-disilahexane

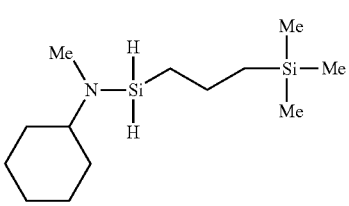

1-cyclohexylmethylamino-5,5-dimethyl-1,5-disilahexane

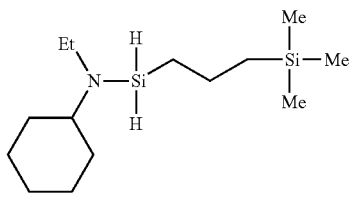

1-cyclohexylethylamino-5,5-dimethyl-1,5-disilahexane

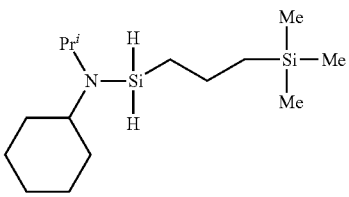

1-cyclohexyl-iso-propylamino-5,5-dimethyl-1,5-disilahexane

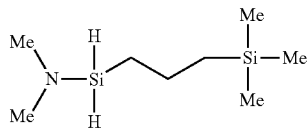

1-dimethylamino-1-methyl-5,5-dimethyl-1,5-disilahexane

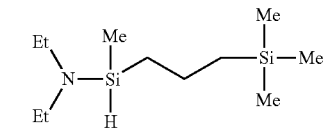

1-diethylamino-1-methyl-5,5-dimethyl-1,5-disilahexane

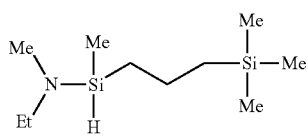

1-ethylmethylamino-1-methyl-5,5-dimethyl-1,5-disilahexane

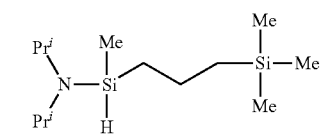

1-di-iso-propylamino-1-methyl-5,5-dimethyl-1,5-disilahexane

TABLE 1-continued

Exemplary Organoaminocarbosilane Compounds of Formula A 1-di-sec-butylamino-1-methyl-5,5-dimethyl-1,5-disilahexane 1-piperindino-1-methyl-5,5-dimethyl-1,5-disilahexane 1-2,6-dimethylpiperindino-1-methyl-5,5-dimethyl-1,5-disilahexane 1-pyrrolidino-1-methyl-5,5-dimethyl-1,5-disilahexane 1-2,5-dimethylpyrrolidino-1-methyl-5,5-dimethyl-1,5-disilahexane 1-cyclohexylmethylamino-1-methyl-5,5-dimethyl-1,5-disilahexane 1-cyclohexylethylamino-1-methyl5,5-dimethyl-1,5-disilahexane 1-cyclohexyl-iso-propylamino-1-methyl-5,5-dimethyl-1,5-disilahexane In the formulas above and throughout the description, the term "alkyl" denotes a linear or branched functional group having from 1 to 10 carbon atoms. Exemplary linear alkyl groups include, but are not limited to, methyl, ethyl, propyl, butyl, pentyl, and hexyl groups. Exemplary branched alkyl groups include, but are not limited to, iso-propyl, iso-butyl, sec-butyl, tert-butyl, iso-pentyl, tert-pentyl, iso-hexyl, and neo-hexyl. In certain embodiments, the alkyl group may have one or more functional groups attached thereto such as, but not limited to, an alkoxy group, a dialkylamino group or combinations thereof, attached thereto. In other embodiments, the alkyl group does not have one or more functional groups attached thereto. The alkyl group may be saturated or, alternatively, unsaturated.

In the formulas above and throughout the description, the term "cyclic alkyl" denotes a cyclic functional group having from 4 to 10 carbon atoms. Exemplary cyclic alkyl groups include, but are not limited to, cyclobutyl, cyclopentyl, cyclohexyl, and cyclooctyl groups.

In the formulas above and throughout the description, the term "alkenyl group" denotes a group which has one or more carbon-carbon double bonds and has from 2 to 10 or from 2 to 10 or from 2 to 6 carbon atoms.

In the formulas above and throughout the description, the term "alkynyl group" denotes a group which has one or more carbon-carbon triple bonds and has from 3 to 10 or from 2 to 10 or from 2 to 6 carbon atoms.

In the formula described herein and throughout the description, the term "dialkylamino group or alkylamino group" denotes a group which has two alkyl groups bonded to a nitrogen atom or one alkyl bonded to a nitrogen atom and has from 1 to 10 or from 2 to 6 or from 2 to 4 carbon atoms. Example include but not limited to HNMe, HNBu$^t$, NMe$_2$, NMeEt, NEt$_2$, NPr$^i{}_2$.

In the formula above and throughout the description, the term "aryl" denotes an aromatic cyclic functional group having from 4 to 10 carbon atoms, from 5 to 10 carbon atoms, or from 6 to 10 carbon atoms. Exemplary aryl groups include, but are not limited to, phenyl, benzyl, chlorobenzyl, tolyl, o-xylyl, 1,2,3-triazolyl, pyrrolyl, and furanyl.

The inventive Formula A can be produced by following reaction equations (1) to (4):

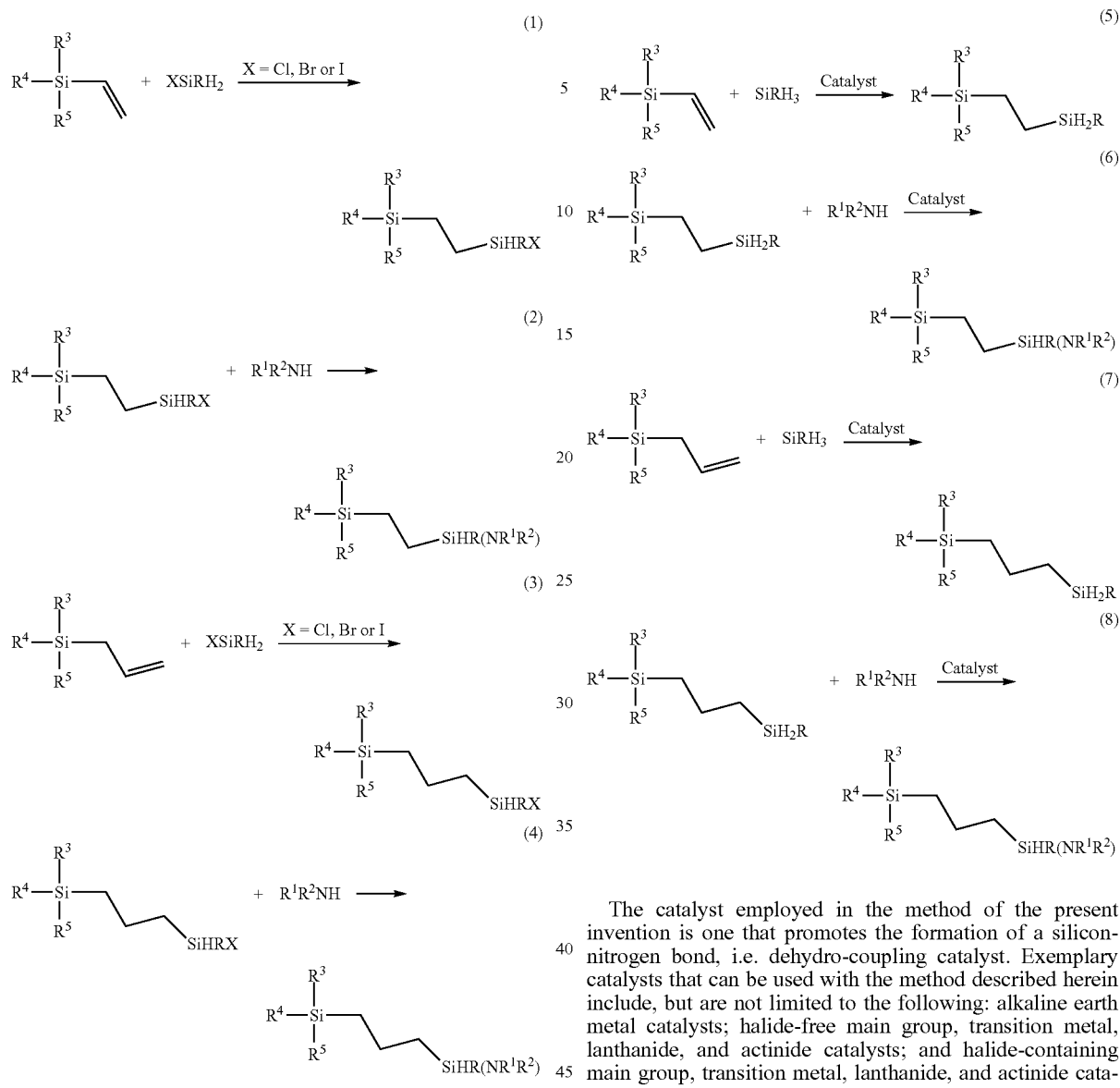

The reaction in Equations (1) to (4) can be conducted with (e.g., in the presence of) or without (e.g., in the absence of) organic solvents. In embodiments wherein an organic solvent is used, examples of suitable organic solvents include, but are not limited to, hydrocarbon such as hexanes, octane, toluene, and ethers such as diethylether and tetrahydrofuran (THF). In these or other embodiments, the reaction temperature is in the range of from about −70° C. to the boiling point of the solvent employed if a solvent is used. The resulting silicon precursor compound can be purified, for example, via vacuum distillation after removing all by-products as well as any solvent(s) if present.

Equations (1) and (4) are exemplary synthetic routes to make the silicon precursor compound having Formula A involving a reaction between halidotrialkylsilane and a primary or secondary amine as described in literatures. Other synthetic routes such as equations (5) to (8) may be also employed to make these silicon precursor compounds having Formula A as disclosed in the prior art.

The catalyst employed in the method of the present invention is one that promotes the formation of a silicon-nitrogen bond, i.e. dehydro-coupling catalyst. Exemplary catalysts that can be used with the method described herein include, but are not limited to the following: alkaline earth metal catalysts; halide-free main group, transition metal, lanthanide, and actinide catalysts; and halide-containing main group, transition metal, lanthanide, and actinide catalysts.

Exemplary alkaline earth metal catalysts include but are not limited to the following: $Mg[N(SiMe_3)_2]_2$, $To^M MgMe$ [$To^M$=tris(4,4-dimethyl-2-oxazolinyl)phenylborate], $To^M Mg$—H, $To^M Mg$—$NR_2$ (R=H, alkyl, aryl) $Ca[N(SiMe_3)_2]_2$, [(dipp-nacnac)CaX(THF)]$_2$ (dipp-nacnac=CH[(CMe)(2,6-$^i$Pr$_2$—$C_6H_3N$)]$_2$; X=H, alkyl, carbosilyl, organoamino), $Ca(CH_2Ph)_2$, $Ca(C_3H_5)_2$, $Ca(\alpha$-$Me_3Si$-2-$(Me_2N)$-benzyl)$_2$(THF)$_2$, $Ca(9$-$(Me_3Si)$-fluorenyl)($\alpha$-$Me_3Si$-2-$(Me_2N)$-benzyl)(THF), [$(Me_3TACD)_3Ca_3(\mu^3$-H)$_2$]$^+$ ($Me_3TACD=Me_3[12]aneN_4$), $Ca(\eta^2$-$Ph_2CNPh)(hmpa)_3$ (hmpa=hexamethylphosphoramide), $Sr[N(SiMe_3)_2]_2$, and other $M^{2+}$ alkaline earth metal-amide, -imine, -alkyl, -hydride, and -carbosilyl complexes (M=Ca, Mg, Sr, Ba).

Exemplary halide-free, main group, transition metal, lanthanide, and actinide catalysts include but are not limited to the following: 1,3-di-iso-propyl-4,5-dimethylimidazol-2-ylidene, 2,2'-bipyridyl, phenanthroline, $B(C_6F_5)_3$, $BR_3$ (R=linear, branched, or cyclic C, to $C_{10}$ alkyl group, a $C_5$ to $C_{10}$ aryl group, or a $C_1$ to $C_{10}$ alkoxy group), $AlR_3$ (R=linear, branched, or cyclic $C_1$ to $C_{10}$ alkyl group, a $C_5$ to $C_{10}$ aryl group, or a $C_1$ to $C_{10}$ alkoxy group), $(C_5H_5)_2TiR_2$ (R=alkyl, H, alkoxy, organoamino, carbosilyl), $(C_5H_5)_2Ti(OAr)_2$ [Ar=(2,6-($^i$Pr)$_2C_6H_3$)], $(C_5H_5)_2Ti(SiHRR')PMe_3$ (wherein R, R' are each independently selected from H, Me, Ph), $TiMe_2$(dmpe)$_2$ (dmpe=1,2-bis(dimethylphosphino)ethane), bis(benzene)chromium(0), $Cr(CO)_6$, $Mn_2(CO)_{12}$, $Fe(CO)_5$, $Fe_3(CO)_{12}$, $(C_5H_5)Fe(CO)_2Me$, $Co_2(CO)_8$, Ni(II) acetate, Nickel(II) acetylacetonate, Ni(cyclooctadiene)$_2$, [(dippe)Ni(µ-H)]$_2$ (dippe=1,2-bis(di-iso-propylphosphino)ethane), (R-indenyl)Ni(PR'$_3$)Me (R=1-$^i$Pr, 1-SiMe$_3$, 1,3-(SiMe$_3$)$_2$; R'=Me,Ph), [{Ni(η-CH$_2$:CHSiMe$_2$)$_2$O}$_2${µ-(η-CH$_2$:CHSiMe$_2$)$_2$O}], Cu(I) acetate, CuH, [tris(4,4-dimethyl-2-oxazolinyl)phenylborate]ZnH, $(C_5H_5)_2ZrR_2$ (R=alkyl, H, alkoxy, organoamino, carbosilyl), $Ru_3(CO)_{12}$, [(Et$_3$P)Ru(2,6-dimesitylthiophenolate)][B[3,5-(CF$_3$)$_2C_6H_3$]$_4$], [$(C_5Me_5)Ru(R_3P)_x(NCMe)_{3-x}$]$^+$ (wherein R is selected from a linear, branched, or cyclic $C_1$ to $C_{10}$ alkyl group and a $C_5$ to $C_{10}$ aryl group; x=0, 1, 2, 3), $Rh_6(CO)_{16}$, tris(triphenylphosphine) rhodium(I)carbonyl hydride, $Rh_2H_2(CO)_2$ (dppm)$_2$ (dppm=bis(diphenylphosphino)methane, $Rh_2$(µ-SiRH)$_2$(CO)$_2$(dppm)$_2$ (R=Ph, Et, $C_6H_{13}$), Pd/C, tris(dibenzylideneacetone)dipalladium(0), tetrakis(triphenylphosphine)palladium(0), Pd(II) acetate, $(C_5H_5)_2SmH$, $(C_5Me_5)_2SmH$, $(THF)_2Yb[N(SiMe_3)_2]_2$, $(NHC)Yb(N(SiMe_3)_2)_2$ [NHC=1,3-bis(2,4,6-trimethylphenyl) imidazol-2-ylidene)], Yb(η$^2$-Ph$_2$CNPh)(hmpa)$_3$ (hmpa=hexamethylphosphoramide), $W(CO)_6$, $Re_2(CO)_{10}$, $Os_3(CO)_{12}$, $Ir_4(CO)_{12}$, (acetylacetonato)dicarbonyliridium(I), Ir(Me)$_2$(C$_5$Me$_5$)L (L=PMe$_3$, PPh$_3$), [Ir(cyclooctadiene)OMe]$_2$, $PtO_2$ (Adams's catalyst), platinum on carbon (Pt/C), ruthenium on carbon (Ru/C), palladium on carbon, nickel on carbon, osmium on carbon, Platinum(0)-1,3-divinyl-1,1,3,3-tetramethyldisiloxane (Karstedt's catalyst), bis(tri-tert-butylphosphine)platinum (0), Pt(cyclooctadiene)$_2$, [(Me$_3$Si)$_2$N]$_3$U][BPh$_4$], [(Et$_2$N)$_3$U][BPh$_4$], and other halide-free M$^{n+}$ complexes (M=Sc, Ti, V, Cr, Mn, Fe, Co, Ni, Cu, Zn, Y, Zr, Nb, Mo, Ru, Rh, Pd, La, Ce, Pr, Nd, Pm, Sm, Eu, Gd, Tb, Dy, Ho, Er, Tm, Yb, Lu, Hf, Ta, W, Re, Os, Ir, Pt, U; n=0, 1, 2, 3, 4, 5, 6).

Exemplary halide-containing, main group, transition metal, lanthanide, and actinide catalysts include but are not limited to the following: $BX_3$ (X=F, Cl, Br, I), $BF_3$.OEt$_2$, $AlX_3$ (X=F, Cl, Br, I), $(C_5H_5)_2TiX_2$ (X=F, Cl), [Mn(CO)$_4$Br]$_2$, $NiCl_2$, $(C_5H_5)_2ZrX_2$ (X=F, Cl), $PdCl_2$, $PdI_2$, CuCl, CuI, $CuF_2$, $CuCl_2$, $CuBr_2$, $Cu(PPh_3)_3Cl$, $ZnCl_2$, [(C$_6$H$_6$)RuX$_2$]$_2$ (X=Cl, Br, I), (Ph$_3$P)$_3$RhCl (Wilkinson's catalyst), [RhCl(cyclooctadiene)]$_2$, di-µ-chloro-tetracarbonyldirhodium(I), bis(triphenylphosphine)rhodium(I) carbonyl chloride, $NdI_2$, $SmI_2$, $DyI_2$, (POCOP)IrHCl (POCOP=2,6-(R$_2$PO)$_2$C$_6$H$_3$; R=$^i$Pr, $^n$Bu, Me), $H_2PtCl_6.nH_2O$ (Speier's catalyst), $PtCl_2$, $Pt(PPh_3)_2Cl_2$, and other halide-containing M$^{n+}$ complexes (M=Sc, Ti, V, Cr, Mn, Fe, Co, Ni, Cu, Zn, Y, Zr, Nb, Mo, Ru, Rh, Pd, La, Ce, Pr, Nd, Pm, Sm, Eu, Gd, Tb, Dy, Ho, Er, Tm, Yb, Lu, Hf, Ta, W, Re, Os, Ir, Pt, U; n=0, 1, 2, 3, 4, 5, 6).

The silicon precursor compounds having Formula A according to the present invention and compositions comprising the silicon precursor compounds having Formula A according to the present invention are preferably substantially free of halide ions. As used herein, the term "substantially free" as it relates to halide ions (or halides) such as, for example, chlorides (i.e. chloride-containing species such as HCl or silicon compounds having at least one Si—Cl bond) and fluorides, bromides, and iodides, means less than 5 ppm (by weight) measured by ICP-MS, preferably less than 3 ppm measured by ICP-MS, and more preferably less than 1 ppm measured by ICP-MS, and most preferably 0 ppm measured by ICP-MS. Chlorides are known to act as decomposition catalysts for the silicon precursor compounds having Formula A. Significant levels of chloride in the final product can cause the silicon precursor compounds to degrade. The gradual degradation of the silicon precursor compounds may directly impact the film deposition process making it difficult for the semiconductor manufacturer to meet film specifications. In addition, the shelf-life or stability is negatively impacted by the higher degradation rate of the silicon precursor compounds thereby making it difficult to guarantee a 1-2 year shelf-life. Therefore, the accelerated decomposition of the silicon precursor compounds presents safety and performance concerns related to the formation of these flammable and/or pyrophoric gaseous byproducts. The silicon precursor compounds having Formula A are preferably substantially free of metal ions such as, $Li^+$, $Al^{3+}$, $Fe^{2+}$, $Fe^{2+}$, $Fe^{3+}$, $Ni^{2+}$, $Cr^{3+}$. As used herein, the term "substantially free" as it relates to Li, Al, Fe, Ni, Cr means less than 5 ppm (by weight), preferably less than 3 ppm, and more preferably less than 1 ppm, and most preferably 0.1 ppm as measured by ICP-MS. In some embodiments, the silicon precursor compounds having Formula A are free of metal ions such as, $Li^+$, $Al^{3+}$, $Fe^{2+}$, $Fe^{3+}$, $Ni^{2+}$, $Cr^{3+}$. As used herein, the term "free of" as it relates to Li, Al, Fe, Ni, Cr, noble metal such as Ru or Pt (ruthenium (Ru) or platinum (Pt) can be impurity from ruthenium or platinum catalysts used in the synthesis), means 0 ppm (by weight) as measured by ICP-MS.

For those embodiments wherein the silicon precursor(s) having Formula A is (are) used in a composition comprising a solvent and silicon precursor compounds having Formula A described herein, the solvent or mixture thereof selected does not react with the silicon precursor. The amount of solvent by weight percentage in the composition ranges from 0.5 wt. % by weight to 99.5 wt. % or from 10 wt. % by weight to 75 wt. %. In this or other embodiments, the solvent has a boiling point (b.p.) similar to the b.p. of the silicon precursor of Formula A or the difference between the b.p. of the solvent and the b.p. of the silicon precursor of Formula A is 40° C. or less, 30° C. or less, or 20° C. or less, or 10° C. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl) ether), or mixtures thereof.

Throughout the description, the term "ALD or ALD-like" refers to a process including, but not limited to, the following processes: a) each reactant including a silicon precursor and a reactive gas is introduced sequentially into a reactor such as a single wafer ALD reactor, semi-batch ALD reactor, or batch furnace ALD reactor; b) each reactant including the silicon precursor and the reactive gas is exposed to a substrate by moving or rotating the substrate to different sections of the reactor and each section is separated by inert gas curtain, i.e., spatial ALD reactor or roll to roll ALD reactor.

In certain embodiments, the silicon oxide or carbon doped silicon oxide films deposited using the methods described herein are formed in the presence of an oxygen-containing source comprising ozone, water ($H_2O$) (e.g., deionized water, purifier water, and/or distilled water), oxygen ($O_2$), oxygen plasma, NO, $N_2O$, $NO_2$, carbon monoxide (CO), carbon dioxide ($CO_2$) and combinations thereof. The oxygen-containing source is passed through, for example, either an in situ or remote plasma generator to provide oxygen-containing plasma source comprising oxygen such as an oxygen plasma, a plasma comprising oxygen and argon, a plasma comprising oxygen and helium, an ozone plasma, a water plasma, a nitrous oxide plasma, or a carbon dioxide plasma. In certain embodiments, the oxygen-containing plasma source comprises an oxygen source gas that is introduced into the reactor at a flow rate ranging from about 1 to about 2000 standard cubic centimeters (sccm) or from about 1 to about 1000 sccm. The oxygen-containing plasma source can be introduced for a time that ranges from about 0.1 to about 100 seconds. In one particular embodiment, the oxygen-containing plasma source comprises water having a temperature of 10° C. or greater. In embodiments wherein the film is deposited by a PEALD or a plasma enhanced cyclic CVD process, the precursor pulse can have a pulse duration that is greater than 0.01 seconds (e.g., about 0.01 to about 0.1 seconds, about 0.1 to about 0.5 seconds, about 0.5 to about 10 seconds, about 0.5 to about 20 seconds, about 1 to about 100 seconds) depending on the ALD reactor's volume, and the oxygen-containing plasma source can have a pulse duration that is less than 0.01 seconds (e.g., about 0.001 to about 0.01 seconds).

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen source, and/or other precursors, source gases, and/or reagents may be performed by changing the time for supplying them to change the stoichiometric composition of the resulting dielectric film.

Energy is applied to the at least one of the silicon precursor, oxygen containing source, or combination thereof to induce reaction and to form the dielectric film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively, a remote plasma-generated process in which plasma is generated outside of the reactor and supplied into the reactor.

The at least one silicon precursor may be delivered to the reaction chamber such as a plasma enhanced cyclic CVD or PEALD reactor or a batch furnace type reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

For those embodiments wherein the at least one silicon precursor described herein is used in a composition comprising a solvent and an at least one silicon precursor described herein, the solvent or mixture thereof selected does not react with the silicon precursor. The amount of solvent by weight percentage in the composition ranges from 0.5 wt. % by weight to 99.5 wt. % or from 10 wt. % by weight to 75 wt. %. In this or other embodiments, the solvent has a boiling point (b.p.) similar to the b.p. of the at least one silicon precursor or the difference between the b.p. of the solvent and the b.p. of the t least one silicon precursor is 40° C. or less, 30° C. or less, or 20° C. or less, or 10° C. or less. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkane (such as octane, nonane, dodecane, ethylcyclohexane), an aromatic hydrocarbon (such as toluene, mesitylene), a tertiary aminoether (such as bis(2-dimethylaminoethyl) ether), or mixtures thereof.

As previously mentioned, the purity level of the at least one silicon precursor is sufficiently high enough to be acceptable for reliable semiconductor manufacturing. In certain embodiments, the at least one silicon precursor described herein comprise less than 2 wt. % by weight, or less than 1 wt. % by weight, or less than 0.5 wt. % by weight of one or more of the following impurities: free amines, free halides or halogen ions, and higher molecular weight species. Higher purity levels of the silicon precursor described herein can be obtained through one or more of the following processes: purification, adsorption, and/or distillation.

In one embodiment of the method described herein, a plasma enhanced cyclic deposition process such as PEALD-like or PEALD may be used wherein the deposition is conducted using the at least one silicon precursor and an oxygen source. The PEALD-like process is defined as a plasma enhanced cyclic CVD process but still provides high conformal silicon oxide films.

In certain embodiments, the gas lines connecting from the precursor canisters to the reaction chamber are heated to one or more temperatures depending upon the process requirements and the container of the at least one silicon precursor is kept at one or more temperatures for bubbling. In other embodiments, a solution comprising the at least one silicon precursor is injected into a vaporizer kept at one or more temperatures for direct liquid injection.

A flow of argon and/or other gas may be employed as a carrier gas to help deliver the vapor of the at least one silicon precursor to the reaction chamber during the precursor pulsing. In certain embodiments, the reaction chamber process pressure is about 50 mTorr to 10 Torr. In other embodiments, the reaction chamber process pressure can be up to 760 Torr (e.g., about 50 mtorr to about 100 Torr).

In a typical PEALD or a PEALD-like process such as a PECCVD process, the substrate such as a silicon oxide substrate is heated on a heater stage in a reaction chamber that is exposed to the silicon precursor initially to allow the complex to chemically adsorb onto the surface of the substrate.

A purge gas such as argon purges away unabsorbed excess complex from the process chamber. After sufficient purging, an oxygen source may be introduced into reaction chamber to react with the absorbed surface followed by another gas purge to remove reaction by-products from the chamber. The process cycle can be repeated to achieve the desired film thickness. In some cases, pumping can replace a purge with inert gas or both can be employed to remove unreacted silicon precursors.

In this or other embodiments, it is understood that the steps of the methods described herein may be performed in a variety of orders, may be performed sequentially, may be performed concurrently (e.g., during at least a portion of another step), and any combination thereof. The respective step of supplying the precursors and the oxygen source gases may be performed by varying the duration of the time for supplying them to change the stoichiometric composition of the resulting dielectric film. Also, purge times after precursor or oxidant steps can be minimized to <0.1 s so that throughput is improved.

One particular embodiment of the method described herein to deposit a high quality silicon oxide film on a substrate comprises the following steps:
a. providing a substrate in a reactor;
b. introducing into the reactor at least one silicon precursor having the Formula A described herein;
c. purging reactor with purge gas to remove at least a portion of the unsorbed precursors;
d. introducing an oxygen-containing plasma source into the reactor and
e. purging reactor with purge gas to remove at least a portion of the unreacted oxygen source,
wherein steps b through e are repeated until a desired thickness of the silicon oxide film is deposited.

Yet another method disclosed herein forms a carbon doped silicon oxide film using a organoaminocarbosilane compound having a structure represented by Formula A as defined above and an oxygen source.

A still further exemplary process is described as follows:
a. providing a substrate in a reactor;
b. contacting vapors generated from an organoaminocarbosilane compound of Formula A described herein with or without co-flowing an oxygen source to chemically sorb the precursors on the heated substrate;
c. purging away any unsorbed precursors;
d. introducing an oxygen source on the heated substrate to react with the sorbed precursors; and,
e. purging away any unreacted oxygen source,
wherein steps b through e are repeated until a desired thickness is achieved.

Various commercial ALD reactors such as single wafer, semi-batch, batch furnace or roll to roll reactor can be employed for depositing the solid silicon oxide or carbon doped silicon oxide.

In some embodiments, the process temperatures for the method described herein use one or more of the following temperatures as endpoints: 0, 25, 50, 75, 100, 125, 150, 175, 200, 225, 250, 275, and 300° C. Exemplary temperature ranges include, but are not limited to the following: from about 0° C. to about 300° C.; or from about 25° C. to about 300° C.; or from about 50° C. to about 290° C.; or from about 25° C. to about 250° C., or from about 25° C. to about 200° C. In other embodiments, the process temperatures for the method described herein use one or more of the following temperatures as endpoints: 350, 325, 350, 375, 400, 425, 450, 475, 500, 525, 550, 575, and 600° C. Exemplary temperature ranges include, but are not limited to the following: from about 300° C. to about 400° C.; or from about 400° C. to about 500° C.; or from about 500° C. to about 600° C.

In another aspect, there is provided a method for depositing a silicon-containing film via flowable chemical vapor deposition (FCVD), the method comprising:

placing a substrate comprising a surface feature into a reactor wherein the substrate is maintained at one or more temperatures ranging from about −20° C. to about 400° C. and a pressure of the reactor is maintained at 100 torr or less;

introducing at least one compound of Formula A:

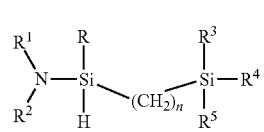

wherein $R^1$ is selected from a linear or branched $C_1$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, a $C_6$ to $C_{10}$ aryl group, a $C_3$ to $C_{10}$ cyclic alkyl group, a branched $C_4$ to $C_{10}$ cyclic alkyl group, a $C_3$ to $C_{10}$ cyclic alkenyl group, a branched $C_4$ to $C_{10}$ cyclic alkenyl group, a $C_3$ to $C_6$ cyclic alkynyl group, a branched $C_3$ to $C_6$ cyclic alkynyl group, a $C_1$ to $C_6$ dialkylamino group; $R^{2-5}$ are independently selected from the group consisting of hydrogen, a linear or branched $C_1$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, a $C_6$ to $C_{10}$ aryl group, a $C_3$ to $C_{10}$ cyclic alkyl group, a branched $C_4$ to $C_{10}$ cyclic alkyl group, a $C_3$ to $C_{10}$ cyclic alkenyl group, a branched $C_4$ to $C_{10}$ cyclic alkenyl group, a $C_3$ to $C_6$ cyclic alkynyl group, a branched $C_3$ to $C_6$ cyclic alkynyl group, and a $C_4$ to $C_{10}$ aryl group; R is selected from hydrogen or methyl; and n=2 or 3;

providing an oxygen source into the reactor to react with the at least one compound to form a film and cover at least a portion of the surface feature;

annealing the film at one or more temperatures of about 100° C. to 1000° C. to coat at least a portion of the surface feature; and treating the substrate with an oxygen source at one or more temperatures ranging from about 20° C. to about 1000° C. to form a silicon-containing film on at least a portion of the surface feature. In certain embodiments, the oxygen source is selected from the group consisting of water vapors, water plasma, ozone, oxygen, oxygen plasma, oxygen/helium plasma, oxygen/argon plasma, nitrogen oxides plasma, carbon dioxide plasma, hydrogen peroxide, organic peroxides, and mixtures thereof. In this or other embodiments, the method steps are repeated until the surface features are filled with the silicon-containing film. In embodiments wherein water vapor is employed as an oxygen source, the substrate temperature ranges from about −20° C. to about 40° C. or from about −10° C. to about 25° C.

In a still further embodiment of the method described herein, the film or the as-deposited film is subjected to a treatment step post film formation. The treatment step can be conducted during at least a portion of the deposition step, after the deposition step, and combinations thereof. Exemplary treatment steps include, without limitation, treatment via high temperature thermal annealing; plasma treatment; ultraviolet (UV) light treatment; laser; electron beam treatment and combinations thereof to affect one or more properties of the film. The films deposited with the silicon precursors having Formula A described herein, when compared to films deposited with previously disclosed silicon precursors under the same conditions, have improved properties such as, without limitation, a wet etch rate that is lower than the wet etch rate of the film before the treatment step or a density that is higher than the density prior to the treatment step. In one particular embodiment, during the deposition process, as-deposited films are intermittently treated. These intermittent or mid-deposition treatments can be performed, for example, after each ALD cycle, after every a certain number of ALD, such as, without limitation, one (1) ALD cycle, two (2) ALD cycles, five (5) ALD cycles, or after every ten (10) or more ALD cycles.

In an embodiment wherein the film is treated with a high temperature annealing step, the annealing temperature is at least 100° C. or greater than the deposition temperature. In this or other embodiments, the annealing temperature ranges from about 400° C. to about 1000° C. In this or other embodiments, the annealing treatment can be conducted in a vacuum (<760 Torr), inert environment or in oxygen containing environment (such as $H_2O$, $N_2O$, $NO_2$ or $O_2$)

In an embodiment wherein the film is treated to UV treatment, film is exposed to broad band UV or, alternatively, an UV source having a wavelength ranging from about 150 nanometers (nm) to about 400 nm. In one particular embodiment, the as-deposited film is exposed to UV in a different chamber than the deposition chamber after a desired film thickness is reached.

In an embodiment where in the film is treated with a plasma, passivation layer such as $SiO_2$ or carbon doped $SiO_2$ is deposited to prevent chlorine and nitrogen contamination to penetrate into film in the subsequent plasma treatment. The passivation layer can be deposited using atomic layer deposition or cyclic chemical vapor deposition.

In an embodiment wherein the film is treated with a plasma, the plasma source is selected from the group consisting of hydrogen plasma, plasma comprising hydrogen and helium, plasma comprising hydrogen and argon. Hydrogen plasma lowers film dielectric constant and boost the damage resistance to following plasma ashing process while still keeping the carbon content in the bulk almost unchanged.

Without intending to be bound by a particular theory, it is believed that the organoaminocarbosilane compound having Formula A as defined above can be anchored via reacting the organoamino group with hydroxyl on substrate surface to provide Si—$(CH_2)_n$—Si fragments wherein the —$(CH_2)_n$— fragment is easily to be removed during subsequent oxidation step, allowing the second silicon atom being anchored on the surface and thus boosting the growth rate of silicon oxide or carbon doped silicon oxide compared to conventional silicon precursors such as bis(tert-butylamino)silane, bis(diethylamino)silane having only one silicon atom.

In certain embodiments, the silicon precursors having Formula A as defined herein can also be used as a dopant for metal containing films, such as but not limited to, metal oxide films or metal nitride films. In these embodiments, the metal containing film is deposited using an ALD or CVD process such as those processes described herein using metal alkoxide, metal amide, or volatile organometallic precursors. Examples of suitable metal alkoxide precursors that may be used with the method disclosed herein include, but are not limited to, group 3 to 6 metal alkoxide, group 3 to 6 metal complexes having both alkoxy and alkyl substituted cyclopentadienyl ligands, group 3 to 6 metal complexes having both alkoxy and alkyl substituted pyrrolyl ligands, group 3 to 6 metal complexes having both alkoxy and diketonate ligands; group 3 to 6 metal complexes having both alkoxy and ketoester ligands; Examples of suitable metal amide precursors that may be used with the method disclosed herein include, but are not limited to, tetrakis (dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino) tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, and combinations thereof. Examples of suitable organometallic precursors that may be used with the method disclosed herein include, but are not limited to, group 3 metal cyclopentadienyls or alkyl cyclopentadienyls. Exemplary Group 3 to 6 metals herein include, but not limited to, Y, La, Ce, Pr, Nd, Sm, Eu, Gd, Tb, Dy, Er, Yb, Lu, Ti, Hf, Zr, V, Nb, Ta, Cr, Mo, and W.

In certain embodiments, the silicon-containing films described herein have a dielectric constant of 6 or less, 5 or less, 4 or less, and 3 or less. In these or other embodiments, the films can have a dielectric constant of about 5 or below, or about 4 or below, or about 3.5 or below. However, it is envisioned that films having other dielectric constants (e.g., higher or lower) can be formed depending upon the desired end-use of the film. An example of silicon-containing film that is formed using the silicon precursors having Formula A precursors and processes described herein has the formulation $Si_xO_yC_zN_vH_w$ wherein Si ranges from about 10 at. % to about 40 at. %; O ranges from about 0 at. % to about 65 at. %; C ranges from about 0 at. % to about 75 at. % or from about 0 at. % to about 50 at. %; N ranges from about 0 at. % to about 75 at. % or from about 0 at. % to 50 at. %; and H ranges from about 0 at. % to about 50 at. % atomic percent weight % wherein x+y+z+v+w=100 atomic weight percent, as determined for example, by XPS or other means. Another example of the silicon containing film that is formed using the organoaminocarbosilanes of Formula A and processes described herein is silicon carbonitride wherein the carbon content is from 1 at % to 80 at % measured by XPS. In yet, another example of the silicon containing film that is formed using the organoaminocarbosilanes of Formula A and processes described herein is amorphous silicon wherein the sum of nitrogen and carbon contents is <10 at. %, preferably <5 at. %, most preferably <1 at. % measured by XPS.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, germanium, germanium-containing, boron-containing, Ga/As, a flexible substrate, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nanoelectromechanical systems, thin film transistor (TFT), light emitting diodes (LED), organic light emitting diodes (OLED), IGZO, and liquid crystal displays (LCD). Potential use of resulting solid silicon oxide or carbon doped silicon oxide include, but not limited to, shallow trench insulation, inter layer dielectric, passivation layer, an etch stop layer, part of a dual spacer, and sacrificial layer for patterning.

The methods described herein provide a high quality silicon oxide or carbon-doped silicon oxide film. The term "high quality" means a film that exhibits one or more of the following characteristics: a density of about 2.1 g/cm$^3$ or greater, 2.2 g/cm$^3$ or greater, 2.25 g/cm$^3$ or greater; a wet etch rate that is 2.5 Å/s or less, 2.0 Å/s or less, 1.5 Å/s or less, 1.0 Å/s or less, 0.5 Å/s or less, 0.1 Å/s or less, 0.05 Å/s or less, 0.01 Å/s or less as measured in a solution of 1:100 of HF to water dilute HF (0.5 wt. % dHF) acid; an electrical leakage of about 1 or less e-8 A/cm$^2$ up to 6 MV/cm); a hydrogen impurity of about 4 e21 at/cm$^3$ or less as measured by SIMS; and combinations thereof. With regard to the etch rate, a thermally grown silicon oxide film has 0.5 Å/s etch rate in 0.5 wt. % diluted HF.

In certain embodiments, one or more silicon precursors having Formula A described herein can be used to form silicon oxide films that are solid and are non-porous or are substantially free of pores.

The following examples illustrate the method for depositing silicon oxide films described herein and are not intended to limit it in any way.

WORKING EXAMPLES

Thermal Atomic Layer Deposition of silicon oxide films were performed on a laboratory scale ALD processing tool. The silicon precursor was delivered to the chamber by vapor draw. All gases (e.g., purge and reactant gas or precursor and oxygen source) were preheated to 100° C. prior to entering the deposition zone. Gases and precursor flow rates were controlled with ALD diaphragm valves with high speed actuation. The substrates used in the deposition were 12-inch-long silicon strips. A thermocouple is attached on the sample holder to confirm substrate temperature. Depositions were performed using ozone as oxygen source gas. Normal deposition process and parameters are shown in Table 2.

TABLE 2

Process for Thermal Atomic Layer Deposition of Silicon Oxide Films with Ozone as Oxygen source on the Laboratory Scale ALD Processing Tool.

| Step 1 | 6 sec | Evacuate reactor | <100 mT |
| Step 2 | variable | Dose Silicon precursor | Reactor pressure typically <2 Torr |
| Step 3 | 6 sec | Purge reactor with nitrogen | Flow 1.5 slpm $N_2$ |
| Step 4 | 6 sec | Evacuate reactor | <100 mT |
| Step 5 | variable | Dose oxygen source ozone | |
| Step 6 | 6 sec | Purge reactor with nitrogen | Flow 1.5 slpm $N_2$ |

All plasma enhanced ALD (PEALD) was performed on a commercial style lateral flow reactor (300 mm PEALD tool manufactured by ASM) equipped with 27.1 MHz direct plasma capability with 3.5 mm fixed spacing between electrodes. The design utilizes outer and inner chambers which have independent pressure settings. The inner chamber is the deposition reactor in which all reactant gases (e.g. precursor, Ar) are mixed in the manifold and delivered to the process reactor. Ar gas is used to maintain reactor pressure in the outer chamber. All precursors were liquids maintained at room temperature in stainless steel bubblers and delivered to the chamber with Ar carrier gas, typically set at 200 sccm flow. All depositions reported in this study were done on native oxide containing Si substrates of 8-12 Ohm-cm. Normal deposition process and parameters are shown in Table 3.

TABLE 3

Process for PEALD Silicon Oxide Deposition in the Commercial Style Lateral Flow PEALD Reactor.

| Step | | |
|---|---|---|
| a | Introduce Si wafer to the reactor | Deposition temperature = 100° or 300° C. |
| b | Introduce silicon precursor to the reactor | Precursor pulse = variable seconds; Carrier gas Argon flow = 200 sccm Process gas Argon flow = 300 sccm Reactor pressure = 2 or 3 Torr |
| c | Purge silicon precursor with inert gas (argon) | Argon flow = 300 sccm Argon flow time = 5 seconds Reactor pressure = 2 or 3 Torr |
| d | Oxidation using plasma | Argon flow = 300 sccm Oxygen flow = 100 sccm Plasma power = variable W Plasma time = variable seconds Reactor pressure = 2 or 3 Torr |
| e | Purge $O_2$ plasma | Plasma off Argon flow = 300 sccm Argon flow time = 2 seconds Reactor pressure = 2 or 3 Torr |

Thickness and refractive indices of the films were measured using a FilmTek 2000SE ellipsometer by fitting the reflection data from the film to a pre-set physical model (e.g., the Lorentz Oscillator model). The growth rate per cycle is calculated by dividing the measured thickness of resulting silicon oxide film by the number of total ALD/PEALD cycles. Wet etch rate (WER) measurements were performed by using 1:99 diluted hydrofluoric (HF) acid solution. Thermal oxide wafers were used as standard for each set of experiments to confirm the etch solution's activity. The samples were all etched for 15 seconds to remove any surface layer before starting to collect the bulk film's WER. A typical thermal oxide wafer wet etch rate for 1:99 dHF water solution was 0.5 Å/s by this procedure. All density measurements were measured by x-ray reflectivity (XRR) method. Compositional analysis was done using secondary ion mass spectrometry (D-SIMS) or X-ray photoelectron spectroscopy (XPS).

Example 1: Synthesis of 1-diethylamino-4,4-dimethyl-1,4-disilapentane

Diethylamine (16.1 g, 0.220 mol), 4,4-dimethyl-disilapentane (20.0 g, 0.151 mol), and $Ru_3(CO)_{12}$ (1.00 g, 0.00156 mol) were combined in a 100 mL round-bottomed flask and stirred for 2 days at room temperature under a nitrogen atmosphere. Gas bubbles were evolved during the reaction. The resulting dark green reaction mixture was placed under vacuum to remove residual volatile starting materials, and then vacuum transferred at 60° C./200 mTorr into a flask cooled to −40° C. The collected liquid (20.6 g) was analyzed by Gas Chromatograph-Mass Spectrometry (GC-MS) and determined to be primarily 1-diethylamino-4,4-dimethyl-1,4-disilapentane. GC-MS showed the following mass peaks: m/z=203 (M+), 188 (M-15), 174, 158, 131, 114, 102, 88, 73, 59, 45.

Example 2: Synthesis of 1-di-iso-propylamino-4,4-dimethyl-1,4-disilapentane

Di-iso-propylamine (99.8 g, 0.986 mol), 4,4-dimethyl-disilapentane (108.8 g, 0.822 mol), and $Ru_3(CO)_{12}$ (5.28 g, 0.00826 mol) were combined in a 500 mL two-necked flask equipped with a magnetic stir bar and reflux condenser. Under the protection of nitrogen atmosphere, the mixture was stirred and heated to 65° C. for 2 hours, during which time gas bubbles were evolved. The reaction temperature was then slowly raised to 100° C. over 2 hours and held there for an additional 2 hours. The resulting dark green reaction mixture was purified by vacuum distillation (68° C./1 Torr) to obtain 165 g of 1-di-iso-propylamino-4,4-dimethyl-1,4-disilapentane as a colorless liquid. GC-MS showed the following mass peaks: m/z=231 (M+), 216, 200, 186, 172, 158, 142, 131, 116, 103, 86, 73, 59, 43.

Comparative Example 3a: PEALD Silicon Oxide Using Dimethylaminotrimethylsilane (DMATMS) Having Only One Silicon Atom Depositions were done with DMATMS as silicon precursor and $O_2$ plasma under conditions given in Table 4. DMATMS as silicon precursor was delivered by vapor draw at ambient temperature (25° C.). The vessel is equipped with orifice with diameter of 0.005" to limit precursor flow.

TABLE 4

PEALD Parameters for Silicon Oxide Using DMATMS

| Step | | |
|---|---|---|
| a | Introduce Si wafer to the reactor | Deposition temperature = 100° C. |
| b | Introduce silicon precursor to the reactor | Precursor pulse = variable seconds; Argon flow = 300 sccm Reactor pressure = 3 Torr |
| c | Purge silicon precursor with inert gas (argon) | Argon flow = 300 sccm Argon flow time = 2 seconds Reactor pressure = 3 Torr |
| d | Oxidation using plasma | Argon flow = 300 sccm Oxygen flow = 100 sccm Plasma power = 200 W Plasma time = 2 seconds Reactor pressure = 3 Torr |
| e | Purge $O_2$ plasma | Plasma off Argon flow = 300 sccm Argon flow time = 0.5 seconds Reactor pressure = 3 Torr |

Steps b to e were repeated 500 times to get a desired thickness of silicon oxide for metrology. With the silicon precursor pulse of 0.5 seconds, film growth rate measured to be 0.83 Å/cycle. With the silicon precursor pulse of 4 seconds, film growth rate measured to be 0.88 Å/cycle, indicating the GPC is saturating with increased precursor pulse time.

Figure 2:
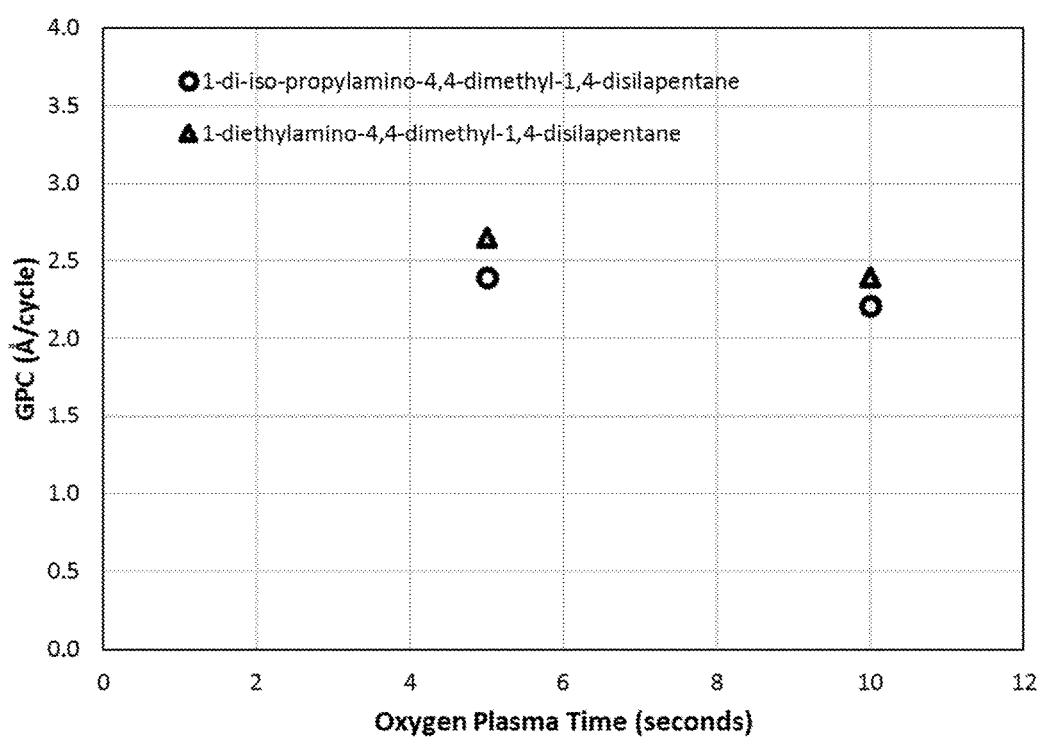
FIG. 2 provides growth rate per cycle (GPC) versus oxygen plasma time using 1-di-iso-propylamino-4,4-dimethyl-1,4-disilapentane and oxygen plasma at temperature of 100° C. described in Example 3, and 1-diethylamino-4,4-dimethyl-1,4-disilapentane and oxygen plasma at temperature of 100° C. described in Example 4, demonstrating both 1-di-iso-propylamino-4,4-dimethyl-1,4-disilapentane and 1-diethylamino-4,4-dimethyl-1,4-disilapentane are suitable for PEALD application

Example 3: PEALD Silicon Oxide Using 1-di-iso-propylamino-4,4-dimethyl-1,4-disilapentane Depositions were performed with 1-di-iso-propylamino-4,4-dimethyl-1,4-disilapentane as silicon precursor and $O_2$ plasma under conditions given in Table 3. Steps b to e were repeated many times to get a desired thickness of silicon oxide for metrology. FIG. 1 shows the GPC with different precursor pulses and FIG. 2 shows the GPC with different oxygen plasma time for precursor 1-di-iso-propylamino-4,4-dimethyl-1,4-disilapentane. From FIG. 1, it can be seen that the GPC is almost constant with 4 seconds and 8 seconds 1-di-iso-propylamino-4,4-dimethyl-1,4-disilapentane precursor pulse, indicating the deposition saturated with 4 seconds of precursor pulse. From FIG. 2, it can be seen that the GPC is slightly decreased with 10 seconds oxygen plasma time compare to 5 seconds oxygen plasma time. The slightly reduced GPC indicates the densification of the film during the longer oxygen plasma time, confirmed by the lower WER and higher film density of film deposited with 10 seconds oxygen plasma time. The results are consistent with ALD deposition behavior. The film deposition parameters and deposition GPC are shown in Table 5. The film properties at different deposition conditions are shown in Table 6.

TABLE 5

PEALD Silicon Oxide Film Deposition Parameters and Deposition GPC by 1-di-iso-propylamino-4,4-dimethyl-1,4-disilapentane

| Process Condition | Dep T (° C.) | Chamber Pressure (Torr) | Reactor Pressure (Torr) | Precursor Flow (s) | Oxygen Plasma Time (s) | Oxygen Plasma Power (w) | GPC (Å/cycle) |
|---|---|---|---|---|---|---|---|
| 1 | 100 | 2.5 | 3 | 4 | 5 | 200 | 2.43 |
| 2 | 100 | 2.5 | 3 | 8 | 5 | 200 | 2.51 |

TABLE 5-continued

PEALD Silicon Oxide Film Deposition Parameters and Deposition GPC by
1-di-iso-propylamino-4,4-dimethyl-1,4-disilapentane

| Process Condition | Dep T (° C.) | Chamber Pressure (Torr) | Reactor Pressure (Torr) | Precursor Flow (s) | Oxygen Plasma Time (s) | Oxygen Plasma Power (w) | GPC (Å/cycle) |
|---|---|---|---|---|---|---|---|
| 3 | 100 | 1.5 | 2 | 4 | 5 | 400 | 2.27 |
| 4 | 100 | 1.5 | 2 | 4 | 5 | 200 | 2.39 |
| 5 | 100 | 1.5 | 2 | 4 | 5 | 100 | 2.54 |
| 6 | 100 | 1.5 | 2 | 4 | 10 | 200 | 2.21 |
| 7 | 300 | 2.5 | 3 | 4 | 5 | 200 | 2.03 |
| 8 | 300 | 2.5 | 3 | 8 | 5 | 200 | 2.11 |
| 9 | 300 | 2.5 | 3 | 12 | 5 | 200 | 2.05 |

TABLE 6

PEALD Silicon Oxide Film Deposition Conditions and Film Properties by
1-di-iso-propylamino-4,4-dimethyl-1,4-disilapentane

| Process Condition | RI | Relative WER to Thermal Oxide | Density (g/cm$^3$) | C content (atoms/cm$^3$) | H content (atoms/cm$^3$) | N content (atoms/cm$^3$) |
|---|---|---|---|---|---|---|
| 1 | 1.46 | 8.5 | 2.20 | | | |
| 2 | 1.46 | 7.2 | 2.15 | | | |
| 3 | 1.47 | 4.2 | 2.21 | 1.66E+19 | 2.26E+21 | 5.46E+19 |
| 4 | 1.47 | 6.6 | 2.05 | 2.00E+19 | 2.93E+21 | 4.49E+19 |
| 5 | 1.46 | 10.6 | 2.22 | 2.47E+19 | 3.65E+21 | 3.13E+19 |
| 6 | 1.47 | 4.3 | 2.19 | 2.50E+19 | 2.44E+21 | 2.10E+20 |
| 7 | 1.46 | 5.1 | | 1.48E+19 | 1.67E+21 | 3.42E+18 |
| 8 | 1.45 | 5.1 | | | | |
| 9 | 1.45 | 5.2 | | | | |

From Table 5, it can be seen that 1-di-iso-propylamino-4,4-dimethyl-1,4-disilapentane gives much higher GPC than DMATMS with only one silicon atom. The film density and WER depends on the process conditions, especially oxygen plasma power and oxygen plasma time. High density and low WER films could be obtained with higher oxygen plasma power and longer oxygen plasma time. Though the precursor has several Si—CH$_3$ and ethylene bridge, the deposited film shows very low carbon impurity levels, close to the detection limit 1 E19 atoms/cm$^3$ of carbon atom, demonstrating ethylene is a good leaving group under oxidation conditions.

Example 4: PEALD Silicon Oxide Using 1-diethylamino-4,4-dimethyl-1,4-disilapentane Depositions was performed with 1-diethylamino-4,4-dimethyl-1,4-disilapentane as silicon precursor and O$_2$ plasma under conditions given in Table 3. Steps b to e were repeated many times to get a desired thickness of silicon oxide for metrology. FIG. 1 shows the GPC with different precursor pulses and FIG. 2 shows the GPC with different oxygen plasma time, including precursor 1-diethylamino-4,4-dimethyl-1,4-disilapentane. From FIG. 1, it can be seen that the GPC is almost constant with 4 seconds and 8 seconds 1-diethylamino-4,4-dimethyl-1,4-disilapentane precursor pulse, indicating the deposition saturated with 4 seconds of precursor pulse. From FIG. 2, it can be seen that the GPC is slightly decreased with 10 seconds oxygen plasma time compare to 5 seconds oxygen plasma time. The slightly reduced GPC indicates the densification of the film during the longer oxygen plasma time, confirmed by the lower WER of film deposited with 10 seconds oxygen plasma time. The results are consistent with ALD deposition behavior. The film deposition parameters and deposition GPC are shown in Table 7. The film properties deposited at different deposition conditions are shown in Table 8.

TABLE 7

PEALD Silicon Oxide Film Deposition Parameters and Deposition GPC by 1-diethylamino-4,4-dimethyl-1,4-disilapentane

| Process condition | Dep T (° C.) | Chamber Pressure (Torr) | Reactor Pressure (Torr) | Precursor Flow (s) | Oxygen Plasma Time (s) | Oxygen Plasma Power (w) | GPC (Å/cycle) |
|---|---|---|---|---|---|---|---|
| 1 | 100 | 2.5 | 3 | 4 | 5 | 200 | 2.70 |
| 2 | 100 | 2.5 | 3 | 8 | 5 | 200 | 2.75 |
| 3 | 100 | 1.5 | 2 | 4 | 5 | 400 | 2.48 |
| 4 | 100 | 1.5 | 2 | 4 | 5 | 200 | 2.64 |
| 5 | 100 | 1.5 | 2 | 4 | 5 | 100 | 2.83 |

TABLE 7-continued

PEALD Silicon Oxide Film Deposition Parameters and Deposition GPC by 1-diethylamino-4,4-dimethyl-1,4-disilapentane

| Process condition | Dep T (° C.) | Chamber Pressure (Torr) | Reactor Pressure (Torr) | Precursor Flow (s) | Oxygen Plasma Time (s) | Oxygen Plasma Power (w) | GPC (Å/cycle) |
|---|---|---|---|---|---|---|---|
| 6 | 100 | 1.5 | 2 | 8 | 5 | 200 | 2.70 |
| 7 | 100 | 1.5 | 2 | 4 | 10 | 200 | 2.39 |

TABLE 8

PEALD Silicon Oxide Film Deposition Conditions and Film Properties by 1-diethylamino-4,4-dimethyl-1,4-disilapentane

| Process Condition | RI | Relative WER to Thermal Oxide | C Content (atom/cm$^3$) | H Content (atom/cm$^3$) | N Content (atom/cm$^3$) |
|---|---|---|---|---|---|
| 1 | 1.44 | 5.71 | | | |
| 2 | 1.44 | 6.41 | 5.78E+18 | 1.81E+21 | 2.60E+19 |
| 3 | 1.44 | 3.69 | 2.17E+19 | 8.62E+20 | 6.80E+18 |
| 4 | 1.44 | 5.71 | 6.76E+18 | 1.48E+21 | 1.80E+19 |
| 5 | 1.44 | 9.09 | 8.67E+18 | 2.16E+21 | 1.45E+19 |
| 6 | 1.43 | 5.93 | 1.07E+19 | 1.55E+21 | 1.27E+19 |
| 7 | 1.45 | 3.73 | 1.99E+19 | 1.68E+21 | 3.33E+19 |

From Table 7, it can be seen that 1-diethylamino-4,4-dimethyl-1,4-disilapentane precursor provides a higher GPC of silicon oxide film than DMATMS having only one silicon atom. The film WER depends on the process conditions, especially oxygen plasma power and oxygen plasma time. Low WER film could be obtained even at 100° C. with higher oxygen plasma power and longer oxygen plasma time. The film shows very low carbon impurities even deposited at 100° C.

Comparative Example 5a: Thermal Atomic Layer Deposition of Silicon Oxide Films with Dimethylaminotrimethylsilane (DMATMS)

Atomic layer deposition of silicon oxide films were conducted using the following precursors DMATMS. The depositions were performed on the laboratory scale ALD processing tool. The silicon precursor was delivered to the chamber by vapor draw. Deposition process and parameters are provided in Table 2. Steps 1 to 6 are repeated until a desired thickness is reached. At 300° C., with the DMATMS precursor dose time of 12 seconds and ozone flow for 10 seconds, the film growth rate per cycle measured is 1.00 Å/cycle and film refractive index is 1.46. At 500° C., with the DMATMS precursor dose time of 12 seconds and ozone flow for 10 seconds, the film growth rate per cycle measured is 1.33 Å/cycle and film refractive index is 1.45.

Example 5: Thermal Atomic Layer Deposition of Silicon Oxide Films with 1-di-iso-propylamino-4,4-dimethyl-1,4-disilapentane Atomic layer deposition of silicon oxide films were conducted using the following precursors: 1-di-iso-propylamino-4,4-dimethyl-1,4-disilapentane. The depositions were performed on the laboratory scale ALD processing tool. The silicon precursor was delivered to the chamber by vapor draw. Deposition process and parameters are provided in Table 2. Steps 1 to 6 are repeated until a desired thickness is reached. The process parameters of the depositions, the deposition GPC and film properties are provided in Table 9 and Table 10.

TABLE 9

Summary of Process Parameters and Results for Thermal Atomic Layer Deposition of Silicon Oxide with 1-di-iso-propylamino-4,4-dimethyl-1,4-disilapentane

| Deposition Temperature (° C.) | Chamber Pressure (Torr) | GPC (Å/cycle) | RI | Relative WER | Density (g/cm$^3$) |
|---|---|---|---|---|---|
| 110 | 0.28 | 1.41 | 1.44 | 6.0 | 1.86 |
| 158 | 0.28 | 1.64 | 1.45 | 11.3 | 1.95 |
| 300 | 0.33 | 2.37 | 1.44 | 13.1 | 1.96 |
| 400 | 0.33 | 2.74 | 1.44 | 8.6 | 2.14 |
| 500 | 0.15 | 2.51 | 1.44 | 6.0 | 2.10 |

TABLE 10

Summary of Process Parameters and Film Composition for Thermal Atomic Layer Deposition of Silicon Oxide with 1-di-iso-propylamino-4,4-dimethyl-1,4-disilapentane

| Deposition Temperature (° C.) | Chamber Pressure (Torr) | XPS C (at. %) | XPS N (at. %) | XPS Si (at. %) | XPS O (at. %) |
|---|---|---|---|---|---|
| 110 | 0.28 | 1.5 | ND | 66.1 | 32.4 |
| 158 | 0.28 | ND | ND | 69.1 | 30.9 |
| 300 | 0.33 | ND | ND | 67.5 | 32.5 |
| 400 | 0.33 | ND | ND | 67.7 | 32.3 |
| 500 | 0.15 | ND | ND | 67.1 | 32.9 |

It can be seen that 1-di-iso-propylamino-4,4-dimethyl-1,4-disilapentane provides a higher GPC than DMATMS, especially at temperature above 300° C., demonstrating the precursors having two silicon atoms can boost the GPC. For films deposited at temperature above 158° C., no carbon was detected in those films, indicating the precursor is good for depositing pure silicon oxide at temperatures 150° C. or higher. The precursor can also provide carbon doped silicon oxide film at deposition temperature of 110° C. The carbon content could be tuned by process conditions, such as ozone concentration, ozone exposure time and deposition temperature. Therefore, by tune process conditions, different kinds of films could be obtained for different applications.

Example 6: Thermal Atomic Layer Deposition of Silicon Oxide Films with 1-diethylamino-4,4-dimethyl-1,4-disilapentane Atomic layer deposition of silicon oxide films were conducted using the following precursors: 1-diethylamino-4,4-dimethyl-1,4-disilapentane. The depositions were performed on the laboratory scale ALD processing tool. The silicon precursor was delivered to the chamber by vapor draw. Deposition process and parameters are provided in Table 2. Steps 1 to 6 are repeated until a desired thickness is reached. The process parameters of the depositions, the growth rate per cycle (GPC) and film properties are provided in Table 11 and 12.

TABLE 11

Summary of Process Parameters and Results for Thermal Atomic Layer Deposition of Silicon Oxide with 1-diethylamino-4,4-dimethyl-1,4-disilapentane

| Deposition Temperature (° C.) | Chamber pressure (Torr) | GPC (Å/cycle) | RI | Relative WER | Density (g/cm³) |
|---|---|---|---|---|---|
| 110 | 0.30 | 1.60 | 1.45 | 2.7 | 1.80 |
| 150 | 0.35 | 2.00 | 1.44 | 5.0 | 1.88 |
| 300 | 0.40 | 2.57 | 1.45 | 10.8 | 2.07 |

TABLE 12

Summary of Process Parameters and Film Composition for Thermal Atomic Layer Deposition of Silicon Oxide with 1-diethylamino-4,4-dimethyl-1,4-disilapentane

| Deposition Temperature (° C.) | Chamber pressure (Torr) | XPS C (at. %) | XPS N (at. %) | XPS Si (at. %) | XPS O (at. %) |
|---|---|---|---|---|---|
| 110 | 0.30 | 2.5 | ND | 65.5 | 32.0 |
| 150 | 0.35 | ND | ND | 67.3 | 32.7 |
| 300 | 0.40 | ND | ND | 65.9 | 34.1 |

It can be seen that 1-diethylamino-4,4-dimethyl-1,4-disilapentane provides a higher GPC than DMATMS, especially at temperatures above 150° C., demonstrating the precursors having two silicon atoms can boost the GPC. For films deposited at temperatures above 150° C., no carbon was detected in those films, indicating the precursor is good for depositing pure silicon oxide at temperatures 150° C. or higher. The precursor can also provide carbon doped silicon oxide film at deposition temperatures of 110° C. or lower. The carbon content could be tuned by process conditions, such as ozone concentration, ozone exposure time and deposition temperature. Therefore, by tuning process conditions, different kinds of films could be obtained for different applications.

The invention claimed is:
1. A method for depositing a film comprising silicon and oxygen onto a substrate, the method comprising the steps of:
  a) providing a substrate in a reactor;
  b) introducing into the reactor at least one silicon precursor compound comprising at least one organoaminocarbosilane compound, wherein the at least one organoaminocarbosilane compound has at least one SiH$_2$ or SiMeH group and is represented by the structure of Formula A:

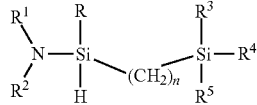

A wherein
  R$^1$ is selected from the group consisting of a linear or branched C$_1$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, a C$_6$ to C$_{10}$ aryl group, a C$_3$ to C$_{10}$ cyclic alkyl group, a branched C$_4$ to C$_{10}$ cyclic alkyl group, a C$_3$ to C$_{10}$ cyclic alkenyl group, a branched C$_4$ to C$_{10}$ cyclic alkenyl group, a C$_3$ to C$_6$ cyclic alkynyl group, a branched C$_3$ to C$_6$ cyclic alkynyl group, a C$_1$ to C$_6$ dialkylamino group, and a C$_1$ to C$_6$ alkylamino group;
  R$^{2-5}$ are each independently selected from the group consisting of hydrogen, a linear or branched C$_1$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, a C$_6$ to C$_{10}$ aryl group, a C$_3$ to C$_{10}$ cyclic alkyl group, a branched C$_4$ to C$_{10}$ cyclic alkyl group, a C$_3$ to C$_{10}$ cyclic alkenyl group, a branched C$_4$ to C$_{10}$ cyclic alkenyl group, a C$_3$ to C$_6$ cyclic alkynyl group, a branched C$_3$ to C$_6$ cyclic alkynyl group, and a C$_4$ to C$_{10}$ aryl group; and
  R is selected from the group consisting of hydrogen and methyl provided that R and R$^{3-5}$ cannot be all hydrogen; and n=2 or 3;
  c) purging the reactor with a purge gas;
  d) introducing an oxygen-containing source into the reactor; and
  e) purging the reactor with a purge gas,
  wherein steps b through e are repeated until a desired thickness of the film is deposited, and
  wherein the method is conducted at one or more temperatures ranging from about 25° C. to 600° C.
2. The method of claim 1, wherein the compound of Formula A is selected from the group consisting of 1-dimethylamino-4,4-dimethyl-1,4-disilapentane, 1-diethylamino-4,4-dimethyl-1,4-disilapentane, 1-ethylmethylamino-4,4-dimethyl-1,4-disilapentane, 1-di-iso-propylamino-4,4-dimethyl-1,4-disilapentane, 1-di-sec-butylamino-4,4-dimethyl-1,4-disilapentane, 1-piperindino-sec-butylamino-4,4-dimethyl-1,4-disilapentane, 1-piperindino-sec-butylamino-4,4-dimethyl-1,4-disilapentane, 1-pyrrolidino-4,4-dimethyl-1,4-disilapentane, 1-2,5-dimethylpyrrolidino-4,4-dimethyl-1,4-disilapentane, 1-cyclohexylmethylamino-4,4-dimethyl-1,4-disilapentane, 1-cyclohexylethylamino-4,4-dimethyl-1,4-disilapentane, 1-cyclohexyl-iso-propylamino-4,4-dimethyl-1,4-disilapentane, 1-dimethylamino-1-methyl-4,4-dimethyl-1,4-disilapentane, 1-dimethylamino-1-methyl-4,4-diethyl-1,4-disilapentane, 1-ethylmethylamino-1-methyl-4,4-dimethyl-1,4-disilapentane, 1-di-iso-propylamino-1-methyl-4,4-dimethyl-1,4-disilapentane, 1-di-sec-butylamino-1-methyl-4,4-dimethyl-1,4-disilapentane, 1-piperindino-1-methyl-4,4-dimethyl-1,4-disilapentane, 1-2,5-dimethylpiperindino-sec-butylamino-1-methyl-4,4-dimethyl-1,4-disilapentane, 1-pyrrolidino-1-methyl-4,4-dimethyl-1,4-disilapentane, 1-2,5-dimethylpyrrolidino-1-methyl-4,4-dimethyl-1,4-disilapentane, 1-cyclohexylmethylamino-1-methyl-4,4-dimethyl-1,4-disilapentane, 1-cyclohexylethylamino-1-methyl-4,4-dimethyl-1,4-disilapentane, 1-cyclohexyl-iso-propylamino-1-methyl-4,4-dimethyl-1,4-disilapentane, 1-dimethylamino-5,5-dimethyl-1,5-disilahexane, 1-diethylamino-5,5-dimethyl-1,5-disilahexane, 1-ethylmethylamino-4,4-dimethyl-4,4-dimethyl-1,5-disilahexane, 1-di-iso-propylamino-5,5-dimethyl-1,5-disilahexane, 1-di-sec-butylamino-5,5-dimethyl-1,5-disilahexane, 1-piperindino-5,5-dimethyl-1,5-disilahexane, 1-2,6-dimethylpiperindino-5, 5-dimethyl-1,5-disilahexane, 1-pyrrolidino-5,5-dimethyl-1,5-disilahexane, 1-2,5-dimethylpyrrolidino-5,5-dimethyl-1,5-disilahexane, 1-cyclohexylmethylamino-5,5-dimethyl-1,5-disilahexane, 1-cyclohexylethylamino-5,5-dimethyl-1,5-disilahexane, 1-cyclohexyl-iso-propylamino-5,5-dimethyl-1,5-disilahexane, 1-dimethylamino-1-methyl-5,5-dimethyl-1,5-disilahexane, 1-diethylamino-1-methyl-5,5-dimethyl-1,5-disilahexane, 1-ethylmethylamino-1-methyl-5,5-dimethyl-1,5-disilahexane, 1-di-iso-propylamino-1-methyl-5,5-dimethyl-1,5-disilahexane, 1-di-sec-butylamino-1-methyl-5,5-dimethyl-1,5-disilahexane, 1-piperindino-1-methyl-5,5-dimethyl-1,5-disilahexane, 1-2,6-dimethylpiperindino-1-methyl-5,5-dimethyl-1,5-disilahexane, 1-pyrrolidino-1-methyl-5,5-dimethyl-1,5-disilahexane, 1-2,5-dimethylpyrrolidino-1-methyl-5,5-dimethyl-1,5-disilahexane, 1-cyclohexylmethylamino-1-methyl-5,5-dimethyl-1,5-disilahexane, 1-cyclohexylethylamino-1-methyl5,5-dimethyl-1,5-disilahexane, and 1-cyclohexyl-iso-propylamino-1-methyl-5,5-dimethyl-1,5-disilahexane.

3. The method of claim 1, wherein the oxygen-containing source is selected from the group consisting of ozone, an oxygen plasma, a plasma comprising oxygen and argon, a plasma comprising oxygen and helium, an ozone plasma, a water plasma, a nitrous oxide plasma, a carbon dioxide plasma, and combinations thereof.

4. The method of claim 1 wherein the oxygen-containing source comprises a plasma.

5. The method of claim 4 wherein the plasma is generated in situ.

6. The method of claim 4 wherein the plasma is generated remotely.

7. The method of claim 4 wherein the film has a density of about 2.0 g/cm$^3$ or greater.

8. The method of claim 1 wherein the film further comprises carbon.

9. The method of claim 8 wherein the film has a density of about 1.8 g/cm$^3$ or greater.

10. The method of claim 8 wherein the carbon content of the film is 0.5 atomic weight percent (at. %) or greater as measured by x-ray photospectroscopy.

11. The method of claim 1 wherein the organoaminocarbosilane compound is substantially free of one or more impurities selected from the group consisting of a halide, metal ions, metal, and combinations thereof.

12. A composition for depositing a silicon oxide film or a carbon doped silicon oxide film using a vapor deposition process, wherein the composition comprises: at least one silicon precursor having a structure represented by Formula A:

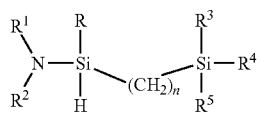

A wherein
R$^1$ is selected from the group consisting of a linear or branched C$_1$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, a C$_6$ to C$_{10}$ aryl group, a C$_3$ to C$_{10}$ cyclic alkyl group, a branched C$_4$ to C$_{10}$ cyclic alkyl group, a C$_3$ to C$_{10}$ cyclic alkenyl group, a branched C$_4$ to C$_{10}$ cyclic alkenyl group, a C$_3$ to C$_6$ cyclic alkynyl group, a branched C$_3$ to C$_6$ cyclic alkynyl group, a C$_1$ to C$_6$ dialkylamino group, and a C$_1$ to C$_6$ alkylamino group;

R$^{2-5}$ are each independently selected from the group consisting of hydrogen, a linear or branched C$_1$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, a C$_6$ to C$_{10}$ aryl group, a C$_3$ to C$_{10}$ cyclic alkyl group, a branched C$_4$ to C$_{10}$ cyclic alkyl group, a C$_3$ to C$_{10}$ cyclic alkenyl group, a branched C$_4$ to C$_{10}$ cyclic alkenyl group, a C$_3$ to C$_6$ cyclic alkynyl group, a branched C$_3$ to C$_6$ cyclic alkynyl group, and a C$_4$ to C$_{10}$ aryl group;

R is selected from the group consisting of hydrogen and methyl; and provided that R and R$^{3-5}$ cannot be all hydrogen; and n=2 or 3.

13. The composition of claim 12, wherein the at least one compound is selected from the group consisting of 1-dimethylamino-4,4-dimethyl-1,4-disilapentane, 1-diethylamino-4,4-dimethyl-1,4-disilapentane, 1-ethylmethylamino-4,4-dimethyl-1,4-disilapentane, 1-di-iso-propylamino-4,4-dimethyl-1,4-disilapentane, 1-di-sec-butylamino-4,4-dimethyl-1,4-disilapentane, 1-piperindino-sec-butylamino-4,4-dimethyl-1,4-disilapentane, 1-piperindino-sec-butylamino-4,4-dimethyl-1,4-disilapentane, 1-pyrrolidino-4,4-dimethyl-1,4-disilapentane, 1-2,5-dimethylpyrrolidino-4,4-dimethyl-1,4-disilapentane, 1-cyclohexylmethylamino-4,4-dimethyl-1,4-disilapentane, 1-cyclohexylethylamino-4,4-dimethyl-1,4-disilapentane, 1-cyclohexyl-iso-propylamino-4,4-dimethyl-1,4-disilapentane, 1-dimethylamino-1-methyl-4,4-dimethyl-1,4-disilapentane, 1-dimethylamino-1-methyl-4,4-diethyl-1,4-disilapentane, 1-ethylmethylamino-1-methyl-4,4-dimethyl-1,4-disilapentane, 1-di-iso-propylamino-1-methyl-4,4-dimethyl-1,4-disilapentane, 1-di-sec-butylamino-1-methyl-4,4-dimethyl-1,4-disilapentane, 1-piperindino-1-methyl-4,4-dimethyl-1,4-disilapentane, 1-2,5-dimethylpiperindino-sec-butylamino-1-methyl-4,4-dimethyl-1,4-disilapentane, 1-pyrrolidino-1-methyl-4,4-dimethyl-1,4-disilapentane, 1-2,5-dimethylpyrrolidino-1-methyl-4,4-dimethyl-1,4-disilapentane, 1-cyclohexylmethylamino-1-methyl-4,4-dimethyl-1,4-disilapentane, 1-cyclohexylethylamino-1-methyl-4,4-dimethyl-1,4-disilapentane, 1-cyclohexyl-iso-propylamino-1-methyl-4,4-dimethyl-1,4-disilapentane, 1-dimethylamino-5,5-dimethyl-1,5-disilahexane, 1-diethylamino-5,5-dimethyl-1,5-disilahexane, 1-ethylmethylamino-4,4-dimethyl-4,4-dimethyl-1,5-disilahexane, 1-di-iso-propylamino-5,5-dimethyl-1,5-disilahexane, 1-di-sec-butylamino-5,5-dimethyl-1,5-disilahexane, 1-piperindino-5,5-dimethyl-1,5-disilahexane, 1-2,6-dimethylpiperindino-5,5-dimethyl-1,5-disilahexane, 1-pyrrolidino-5,5-dimethyl-1,5-disilahexane, 1-2,5-dimethylpyrrolidino-5,5-dimethyl-1,5-disilahexane, 1-cyclohexylmethylamino-5,5-dimethyl-1,5-disilahexane, 1-cyclohexylethylamino-5,5-dimethyl-1,5-disilahexane, 1-cyclohexyl-iso-propylamino-5,5-dimethyl-1,5-disilahexane, 1-dimethylamino-1-methyl-5,5-dimethyl-1,5-disilahexane, 1-diethylamino-1-methyl-5,5-dimethyl-1,5-disilahexane, 1-ethylmethylamino-1-methyl-5,5-dimethyl-1,5-disilahexane, 1-di-iso-propylamino-1-methyl-5,5-dimethyl-1,5-disilahexane, 1-di-sec-butylamino-1-methyl-5,5-dimethyl-1,5-disilahexane, 1-piperindino-1-methyl-5,5-dimethyl-1,5-disilahexane, 1-2,6-dimethylpiperindino-1-methyl-5,5-dimethyl-1,5-disilahexane, 1-pyrrolidino-1-methyl-5,5-dimethyl-1,5-disilahexane, 1-2,5-dimethylpyrrolidino-1-methyl-5,5-dimethyl-1,5-disilahexane, 1-cyclohexylmethylamino-1- methyl-5,5-dimethyl-1,5-disilahexane, 1-cyclohexylethylamino-1-methyl5,5-dimethyl-1,5-disilahexane, 1-cyclohexyl-iso-propylamino-1-methyl-5,5-dimethyl-1,5-disilahexane, and combinations thereof.

14. The composition of claim 12, wherein the composition is substantially free of halides.

15. The composition of claim 14, wherein the composition is substantially free of chloride ions and the concentration of chloride ions is less than 50 ppm measured by ICP-MS.

16. The composition of claim 15, wherein the chloride ion concentration is less than 10 ppm measured by ICP-MS.

17. The composition of claim 16, wherein the chloride ion concentration is less than 5 ppm measured by ICP-MS.

18. The composition of claim 12 wherein the composition is substantially free of one or more impurities selected from the group consisting of a halide, metal ions, metal, and combinations thereof.

19. A film obtained by the method of claim 1.

20. The film of claim 19 comprising at least one of the following characteristics: a density of at least about 2.0 g/cm$^3$; a wet etch rate that is less than about 2.5 Å/s as measured in a solution of 1:100 of HF to water (0.5 wt. % dHF) acid; an electrical leakage of less than about 1 e-8 Å/cm$^2$ up to 6 MV/cm; and a hydrogen impurity of less than about 4 e 21 at/cc as measured by SIMS.

* * * * *